United States Patent
Yang et al.

(10) Patent No.: US 6,713,476 B2
(45) Date of Patent: Mar. 30, 2004

(54) SUBSTITUTED CYCLOALKYLS AS INHIBITORS OF A BETA PROTEIN PRODUCTION

(75) Inventors: Michael G Yang, Wilmington, DE (US); Hong Liu, Glen Mills, PA (US)

(73) Assignee: Dupont Pharmaceuticals Company, Wilmington, DE (US)

(*) Notice: Subject to any disclaimer, the term of this patent is extended or adjusted under 35 U.S.C. 154(b) by 0 days.

(21) Appl. No.: 09/824,945

(22) Filed: Apr. 3, 2001

(65) Prior Publication Data

US 2002/0061874 A1 May 23, 2002

Related U.S. Application Data

(60) Provisional application No. 60/194,302, filed on Apr. 3, 2000.

(51) Int. Cl.[7] ............... C07D 223/18; C07D 243/24; C07D 243/14; A61K 31/55; A61P 25/28
(52) U.S. Cl. ............... 514/221; 540/509
(58) Field of Search ............... 540/509; 514/221

(56) References Cited

U.S. PATENT DOCUMENTS

| | | | |
|---|---|---|---|
| 5,283,241 A | | 2/1994 | Bochis et al. ............... 514/183 |
| 5,426,185 A | * | 6/1995 | Baldwin et al. ............ 540/509 |
| 5,532,359 A | | 7/1996 | Marsters et al. ............ 540/522 |
| 5,550,126 A | | 8/1996 | Horwell et al. ........... 514/237.5 |
| 5,578,629 A | | 11/1996 | Ciccarone et al. .......... 514/397 |
| 5,595,990 A | | 1/1997 | Baldwin et al. ............ 514/221 |
| 5,602,145 A | | 2/1997 | Samanen ................. 514/309 |
| 5,618,812 A | | 4/1997 | Pineiro et al. ............. 514/221 |
| 5,672,596 A | | 9/1997 | Wyvratt et al. ............ 514/183 |
| 5,710,153 A | | 1/1998 | Ohmoto et al. ............ 514/236.2 |
| 5,710,171 A | | 1/1998 | Dinsmore et al. .......... 514/396 |
| 5,756,528 A | | 5/1998 | Anthony et al. ............ 514/399 |
| 5,763,437 A | | 6/1998 | Sato et al. ................. 514/221 |
| 5,817,658 A | | 10/1998 | Siegl et al. ................ 514/221 |
| 5,852,010 A | | 12/1998 | Graham et al. ............ 514/221 |
| 5,856,326 A | | 1/1999 | Anthony et al. ............ 514/252 |
| 5,859,012 A | | 1/1999 | Dinsmore et al. .......... 514/252 |
| 5,869,682 A | | 2/1999 | DeSolms ................. 548/335.5 |
| 5,872,135 A | | 2/1999 | DeSolms ................. 514/326 |
| 5,885,995 A | | 3/1999 | Dinsmore ................. 514/252 |
| 5,891,889 A | | 4/1999 | Anthony et al. ............ 514/326 |
| 5,905,077 A | | 5/1999 | Jungheim et al. ......... 514/222.2 |
| 5,919,785 A | | 7/1999 | Dinsmore et al. .......... 514/252 |
| 5,936,089 A | | 8/1999 | Carpino et al. ............ 546/183 |
| 5,965,578 A | | 10/1999 | Graham et al. ............ 514/326 |

FOREIGN PATENT DOCUMENTS

| | | |
|---|---|---|
| EP | 0421802 | 4/1991 |
| EP | 0434360 | 6/1991 |
| EP | 0842944 | 5/1998 |
| WO | WO 9216524 | 10/1992 |
| WO | WO 9217460 | 10/1992 |
| WO | WO 3403437 | 2/1994 |
| WO | WO 9405634 | 3/1994 |
| WO | WO 9414776 | 7/1994 |
| WO | WO 9509633 | 4/1995 |
| WO | WO 9617833 | 6/1996 |
| WO | WO 9618602 | 6/1996 |
| WO | WO 9620918 | 7/1996 |
| WO | WO 9633165 | 10/1996 |
| WO | WO 9639137 | 12/1996 |
| WO | WO 9719053 | 5/1997 |
| WO | WO 9727852 | 8/1997 |
| WO | WO 9736877 | 10/1997 |
| WO | WO 9736879 | 10/1997 |
| WO | WO 9736900 | 10/1997 |
| WO | WO 9738664 | 10/1997 |
| WO | WO 9745412 | 12/1997 |
| WO | WO 9816523 | 4/1998 |
| WO | WO 9822430 | 5/1998 |
| WO | WO 9822433 | 5/1998 |
| WO | WO 9822441 | 5/1998 |

(List continued on next page.)

OTHER PUBLICATIONS

Dingwall; J. Clinical Invest., 108, Nov. 2001, 1243–1246.

Selkoe; J. Alzheimer's Disease, Mar., 2001, p. 75–81.

Tanzi and Parson, "Decoding Darkness, The Search for the Genetic Causes of Alzheimer's Disease", Perseus Publishing, 2000, pp. xvii–xviii.

Olson et al., Current Opinion in Drug Discovery and Development, 4, 2001, p. 390–401.

Hansen, T.K. et al, "Naphtho–fused azepines as potent growth hormone secretagogues" Bioorganic & Medicinal Chem. Letters, vol. 7, No. 23, Dec. 2, 1997, p. 2951–2954.

*Primary Examiner*—Bruck Kifle
(74) *Attorney, Agent, or Firm*—Stephen B. Davis

(57) ABSTRACT

This invention relates to novel lactams having the Formula (I):

(I)

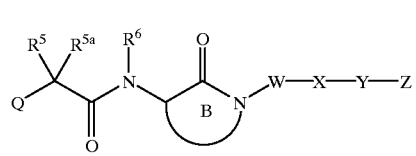

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

30 Claims, No Drawings

U.S. PATENT DOCUMENTS

| | | |
|---|---|---|
| WO | WO 9822493 | 5/1998 |
| WO | WO 9827053 | 6/1998 |
| WO | WO 9828268 | 7/1998 |
| WO | WO 9828980 | 7/1998 |
| WO | WO 9837079 | 8/1998 |
| WO | WO 9841510 | 9/1998 |
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9966934 | 12/1999 |
| WO | WO 9967219 | 12/1999 |
| WO | WO 9967220 | 12/1999 |
| WO | WO 9967221 | 12/1999 |
| WO | WO 0007995 | 2/2000 |
| WO | WO 0028331 | 5/2000 |
| WO | WO 0038618 | 7/2000 |
| WO | WO 0119797 | 3/2001 |
| WO | WO 0160826 | 8/2001 |

* cited by examiner

SUBSTITUTED CYCLOALKYLS AS INHIBITORS OF A BETA PROTEIN PRODUCTION

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review see, Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. β is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γsecretase activity, either directly or indirectly, could control the production of Aβ. Advantageously, compounds that specifically target γ secretases, could control the production of Aβ. Such inhibition of β or γsecretases could thereby reduce production of Aβ, which, thereby, could reduce or prevent the neurological disorders associated with Aβ protein.

PCT publication number WO 96/29313 discloses the general formula:

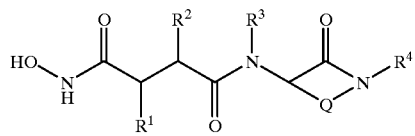

covering metalloprotease inhibiting compounds useful for the treatment of diseases associated with excess and/or unwanted matrix metalloprotease activity, particularly collagenase and or stromelysin activity.

Compounds of general formula:

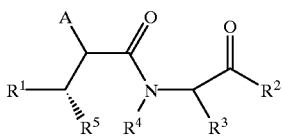

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

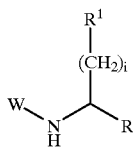

and discloses compounds that are protease inhibitors that inhibit Aβ production.

U.S. Pat. No. 5,703,129 discloses the general formula:

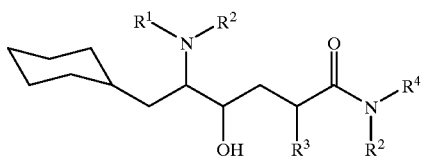

which covers 5-amino-6-cyclohexyl-4-hydroxy-hexanamide derivatives that inhibit Aβ production and are useful in the treatment of Alzheimer's disease.

Copending, commonly assigned U.S. patent application Ser. No. 09/370,089 filed Aug. 7, 1999 (equivalent to international application PCT US99/17717) discloses lactams of general formula:

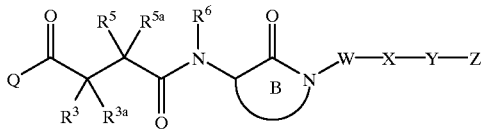

wherein the lactam ring B is substituted by succinamide and a carbocyclic, aryl, or heteroaryl group. These compounds inhibit the processing of amyloid precursor protein and, more specifically, inhibit the production of Aβ-peptide, thereby acting to prevent the formation of neurological deposits of amyloid protein.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors discovery that compounds of Formula (I):

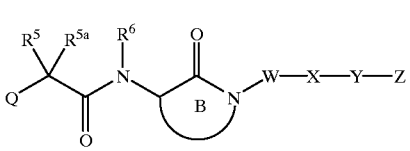

or pharmaceutically acceptable salt or prodrug forms thereof, wherein $R^3$, $R^{3a}$, $R^5$, $R^{5a}$, $R^6$, Q, B, W, X, Y, and Z are defined below, are effective inhibitors of the production of Aβ protein.

DETAILED DESCRIPTION OF PREFERRED EMBODIMENTS

Thus, in a first embodiment, the present invention provides a novel compound of Formula (I):

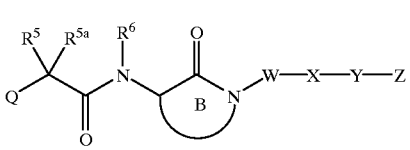

or a stereoisomer, pharmaceutically acceptable salt or prodrug thereof, wherein:

Q is
—$(CR^7R^{7a})_m$—$R^4$,
—$(CR^7R^{7a})_m$—CH(OH)—$R^4$,
—$(CR^7R^{7a})_m$m—NHC(=O)—$R^4$,
—$(CR^7R^{7a})_n$—S—$R^4$,
—$(CR^7R^{7a})_n$—O—$R^4$,
—$(CR^7R^{7a})_n$—N($R^{7b}$)—$R^4$,
—$(CR^7R^{7a})_n$—S(=O)—$R^4$,
—$(CR^7R^{7a})_n$—S(=O)$_2$—$R^4$, or
—$(CR^7R^{7a})_n$—C(=O)—$R^4$;
m is 1, 2, or 3;
n is 0, 1, or 2;
$R^4$ is H,
$C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from H, OH, F, Cl, Br, I, $CF_3$, $C_1$–$C_3$ alkyl,
$C_3$–$C_{10}$ carbocycle substituted with 0–3 $R^{4b}$,
$C_6$–$C_{10}$ aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl,
$C_1$–$C_4$ haloalkoxy, and $C_1$–$C_4$ haloalkyl-S—;

$R^5$ and $R^{5a}$ are combined to form a 3–8 membered carbocyclic moiety;
  wherein said 3–8 membered carbocyclic moiety is saturated or partially unsaturated;
  wherein said 3–8 membered carbocyclic moiety may optionally contain a heteroatom selected from —O—, —S—, —S(=O)—, —S(=O)$_2$—, —N=, —NH—, and —N($R^{20}$)—; and
  wherein said 3–8 membered carbocyclic moiety is substituted with 0–4 $R^{5b}$;

additionally, two $R^{5b}$ substituents on adjacent atoms may be combined to form a benzo fused radical; wherein said benzo fused radical is substituted with 0–4 $R^{23}$;

additionally, two $R^{5b}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^{5b}$ substituents on the same or adjacent carbon atoms may be combined to form a $C_3$–$C_6$ carbocycle substituted with 0–3 $R^{23}$;

$R^{5b}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_6$ carbocycle, phenyl, and a 5 to 6 membered heterocycle containing 1 to 4 heteroatoms selected from nitrogen, oxygen, and sulphur;

$R^6$ is H;
  $C_1$–$C_6$ alkyl substituted with 0–3 $R^{6a}$;
  $C_3$–$C_{10}$ carbocycle substituted with 0–3 $R^{6b}$; or
  $C_6$–$C_{10}$ aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl and $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

$R^{7a}$, at each occurrence, is independently H or $C_1$–$C_4$ alkyl;

$R^{7a}$, at each occurrence, is independently H or $C_1$–$C_4$ alkyl;

$R^{7b}$ is H, $C_1$–$C_4$ alkyl, or ($C_1$–$C_4$ alkyl)OC(=O)—;

Ring B is a 7 membered lactam,
  wherein the lactam is saturated, partially saturated or unsaturated;
  wherein each additional lactam carbon is substituted with 0–2 $R^{11}$; and,
  optionally, the lactam contains a heteroatom selected from —O—, —S—, —S(=O)—, —S(=O)$_2$—, —N=, —NH—, and —N($R^{10}$)—;

additionally, two $R^{11}$ substituents on adjacent atoms may be combined to form a benzo fused radical; wherein said benzo fused radical is substituted with 0–4 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;

additionally, two $R^{11}$ substituents on the same or adjacent carbon atoms may be combined to form a $C_3$–$C_6$ carbocycle substituted with 0–3 $R^{13}$;

$R^{10}$ is H, C(=O)$R^{17}$, C(=O)O$R^{17}$, C(=O)$NR^{18}R^{19}$, $S(=O)_2NR^{18}R^{19}$, $S(=O)_2R^{17}$;
  $C_1$–$C_6$ alkyl optionally substituted with 0–3 $R^{10a}$;
  $C_6$–$C_{10}$ aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from: H, $C_1$–$C_6$ alkyl, $OR^{14}$, Cl, F, Br, I, =O, CN, $N_2$, $NR^{15}R^{16}$, $CF_3$;
  aryl substituted with 0–4 $R^{10b}$;
  $C_3$–$C_{10}$ carbocycle substituted with 0–3 $R^{10b}$; and
  5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10b}$, at each occurrence, is independently selected from H,
  OH, Cl, F, Br, I, CN, $N_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, C(=O)$R^{17}$, C(=O)O$R^{17}$, C(=O)$NR^{18}R^{19}$, $S(=O)_2NR^{18}R^{19}$, $CF_3$;
  $C_1$–$C_6$ alkyl optionally substituted with 0–3 $R^{11a}$;
  $C_6$–$C_{10}$ aryl substituted with 0–3 $R^{11b}$;
  $C_3$–$C_{10}$ carbocycle substituted with 0–3 $R^{11b}$; and
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
  phenyl substituted with 0–3 $R^{11b}$;
  $C_3$–$C_6$ cycloalkyl substituted with 0–3 $R^{11b}$; and
  5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H,
  OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$–$C_6$ alkyl, $C_1$–$C_4$ alkoxy, $C_1$–$C_4$ haloalkyl,
  $C_1$–$C_4$ haloalkoxy, and $C_1$–$C_4$ haloalkyl-S—;

W is a bond or —(C$R^8R^{8a}$)$_p$—;
p is 0, 1, 2, 3, or 4;
$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;

X is a bond;
  $C_6$–$C_{10}$ aryl substituted with 0–3 $R^{Xb}$;
  $C_3$–$C_{10}$ carbocycle substituted with 0–3 $R^{Xb}$; or
  5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S($=$O)CH$_3$, S($=$O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;

t is 0, 1, or 2;

u is 0, 1, or 2;

R$^9$ and R$^{9a}$, at each occurrence, are independently selected from H, F, C$_1$–C$_6$ alkyl or C$_3$–C$_8$ cycloalkyl;

V is a bond, —C($=$O)—, —O—, —S—, —S($=$O)—, —S($=$O)$_2$—, —N(R$^{19}$)—, —C($=$O)NR$^{19b}$—, —NR$^{19b}$C($=$O)—, —NR$^{19b}$S($=$O)$_2$—, —S($=$O)$_2$NR$^{19b}$—, —NR$^{19b}$S($=$O)—, —S($=$O)NR$^{19}$—, —C($=$O)O—, or —OC($=$O)—;

Z is H;

C$_1$–C$_8$ alkyl substituted with 0–3 R$^{12a}$;

C$_2$–C$_6$ alkenyl substituted with 0–3 R$^{12a}$;

C$_2$–C$_6$ alkynyl substituted with 0–3 R$^{12a}$;

C$_6$–C$_{10}$ aryl substituted with 0–4 R$^{12b}$;

C$_3$–C$_{10}$ carbocycle substituted with 0–4 R$^{12b}$; or 5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C($=$O)NR$^{15}$R$^{16}$, CF$_3$, acetyl, SCH$_3$, S($=$O)CH$_3$, S($=$O)$_2$CH$_3$, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—, C$_6$–C$_{10}$ aryl substituted with 0–4 R$^{12b}$;

C$_3$–C$_{10}$ carbocycle substituted with 0–4 R$^{12b}$; and 5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S($=$O)CH$_3$, S($=$O)$_2$CH$_3$, aryl, C$_3$–C$_6$ cycloalkyl, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{13}$, at each occurrence, is independently selected from H, OH, C$_1$–C$_6$ alkyl, C$_1$–C$_4$ alkoxy, Cl, F, Br, I, CN, N$_2$, NR$^{15}$R$^{16}$, and CF$_3$;

R$^{14}$ is H, phenyl, benzyl, C$_1$–C$_6$ alkyl, C$_2$–C$_6$ alkoxyalkyl, or

C$_3$–C$_6$ cycloalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, (C$_1$–C$_6$ alkyl)—C($=$O)—, and (C$_1$–C$_6$ alkyl)—S($=$O)$_2$—;

R$^{16}$, at each occurrence, is independently selected from H, OH, C$_1$–C$_6$ alkyl, benzyl, phenethyl, (C$_1$–C$_6$ alkyl)—C($=$O)—, and (C$_1$–C$_6$ alkyl)—S($=$O)$_2$—;

R$^{17}$ is H, C$_1$–C$_6$ alkyl, C$_2$–C$_6$ alkoxyalkyl, aryl substituted by 0–4 R$^{17a}$, or —CH$_2$-aryl substituted by 0–4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$–C$_4$ haloalkyl;

R$^{18}$, at each occurrence, is independently selected from H, C$_1$–C$_6$ alkyl, aryl, aryl-CH$_2$—, aryl-CH$_2$CH$_2$—, (C$_1$–C$_6$ alkyl)—C($=$O)—, and (C$_1$–C$_6$ alkyl)—S($=$O)$_2$—;

R$^{19}$, at each occurrence, is independently selected from H, OH, C$_1$–C$_6$ alkyl, aryl, aryl-CH$_2$—, aryl-CH$_2$CH$_2$—, (C$_1$–C$_6$ alkyl)—C($=$O)—, and (C$_1$–C$_6$ alkyl)—S($=$O)$_2$—;

R$^{19b}$, at each occurrence, is independently is H or C$_1$–C$_4$ alkyl;

R$^{20}$ is H, C($=$O)R$^{17}$, C($=$O)OR$^{17}$, C($=$O)NR$^{18}$R$^{19}$, S($=$O)$_2$NR$^{18}$R$^{19}$, S($=$O)$_2$R$^{17}$;

C$_1$–C$_6$ alkyl optionally substituted with 0–3 R$^{20a}$; or

C$_6$–C$_{10}$ aryl substituted with 0–4 R$^{20b}$;

R$^{20a}$, at each occurrence, is independently selected from H, C$_1$–C$_4$ alkyl, OR$^{14}$, Cl, F, Br, I, $=$O, CN, NO$_2$, NR$^{15}$R$^{16}$, CF$_3$, and aryl substituted with 0–4 R$^{20b}$;

R$^{20b}$, at each occurrence, is independently selected from H, OH, Cl, F, Br, I, CN, NO$_2$, NR$^{15}$R$^{16}$, CF$_3$, acetyl, SCH$_3$, S($=$O)CH$_3$, S($=$O)$_2$CH$_3$, C$_1$–C$_4$ alkyl, C$_1$–C$_4$ alkoxy, C$_1$–C$_4$ haloalkyl, C$_1$–C$_4$ haloalkoxy, and C$_1$–C$_4$ haloalkyl-S—; and R$^{23}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

provided when Q is —(CR$^7$R$^{7a}$)$_n$—N(R$^{7b}$)—R$^4$ and R$^{7b}$ is (C$_1$–C$_4$alkyl)OC($=$O)—, then n is 1 or 2; and provided when Q is —(CR$^7$R$^{7a}$)$_n$—N(R$^{7b}$)—R$^4$ and n is 0, then R$^4$ does not contain a —C($=$O)— adjacent to —N(R$^{7b}$)—.

[2] In a preferred embodiment the present invention provides for a compound of Formula (I) or a stereoisomer, pharmaceutically acceptable salt or prodrug thereof, wherein:

Q is

—(CR$^7$R$^{7a}$)$_m$—R$^4$,

—(CR$^7$R$^{7a}$)$_m$—CH(OH)—R$^4$,

—(CR$^7$R$^{7a}$)$_m$—NHC($=$O)—R$^4$,

—(CR$^7$R$^{7a}$)$_n$—S—R$^4$,

—(CR$^7$R$^{7a}$)$_n$—O—R$^4$, or

—(CR$^7$R$^{7a}$)$_n$—N(R$^{7b}$)—R$^4$;

m is 1 or 2;

n is 0 or 1;

R$^4$ is H,

C$_1$–C$_8$ alkyl substituted with 0–3 R$^{4a}$,

C$_2$–C$_8$ alkenyl substituted with 0–3 R$^{4a}$,

C$_2$–C$_8$ alkynyl substituted with 0–3 R$^{4a}$,

C$_3$–C$_{10}$ carbocycle substituted with 0–3 R$^{4b}$,

C$_6$–C$_{10}$ aryl substituted with 0–3 R$^{4b}$, or 5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4a}$, at each occurrence, is independently selected from H, OH, F, Cl, Br, I, CF$_3$, C$_1$–C$_3$ alkyl, C$_3$–C$_{10}$ carbocycle substituted with 0–3 R$^{4b}$, C$_6$–C$_{10}$ aryl substituted with 0–3 R$^{4b}$, and 5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S($=$O)CH$_3$, S($=$O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^5$ and R$^{5a}$ are combined to form a 3–8 membered carbocyclic moiety;

wherein said 3–8 membered carbocyclic moiety is saturated or partially unsaturated;

wherein said 3–8 membered carbocyclic moiety may optionally contain a heteroatom selected from —O—, —NH—, and —N(R$^{20}$)—; and wherein said 3–8 membered carbocyclic moiety is substituted with 0–4 $R^{5b}$;

additionally, two $R^{5b}$ substituents on adjacent atoms may be combined to form a benzo fused radical; wherein said benzo fused radical is substituted with 0–4 $R^{23}$;

additionally, two $R^{5b}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^{5b}$ substituents on the same or adjacent carbon atoms may be combined to form a $C_3$–$C_6$ carbocycle substituted with 0–3 $R^{23}$;

$R^{5b}$, at each occurrence, is independently selected from H, OH, Cl, F, Br, I, CN, $N_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, $C_1$–$C_4$ haloalkyl-S—, $C_3$–$C_6$ carbocycle, phenyl, and a 5 to 6 membered heterocycle containing 1 to 4 heteroatoms selected from nitrogen, oxygen, and sulphur;

$R^6$ is H, methyl, or ethyl;

$R^7$ at each occurrence, is independently H or $C_1$–$C_4$ alkyl;

$R^{7a}$, at each occurrence, is independently H or $C_1$–$C_4$ alkyl;

$R^{7b}$ is H, $C_1$–$C_4$ alkyl, or ($C_1$–$C_4$ alkyl)OC(=O)—;

Ring B is selected from:

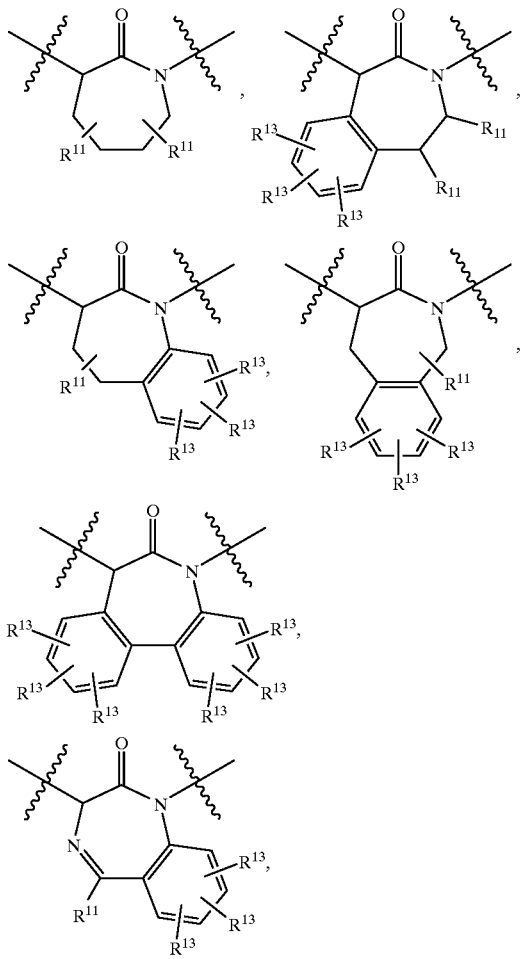

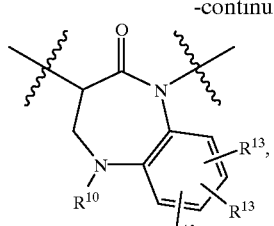

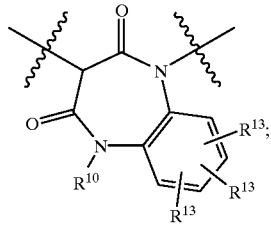

$R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;

$C_1$–$C_6$ alkyl optionally substituted with 0–3 $R^{10a}$;

$C_6$–$C_{10}$ aryl substituted with 0–4 $R^{10b}$;

$C_3$–$C_{10}$ carbocycle substituted with 0–3 $R^{10b}$; or 5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from: H, $C_1$–$C_6$ alkyl, $OR^{14}$, Cl, F, Br, I, =O, CN, $NO_2$, $NR^{15}R^{16}$, $CF_3$;

aryl substituted with 0–4 $R^{10b}$;

$C_3$–$C_{10}$ carbocycle substituted with 0–3 $R^{10b}$; and 5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_{1-C4}$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $N_2$, $NR^{18}R^{19}$, C(=O)$R^{17}$, C(=O)O$R^{17}$, C(=O)N$R^{18}R^{19}$, S(=O)$_2$N$R^{18}R^{19}$, $CF_3$;

$C_1$–$C_6$ alkyl optionally substituted with 0–3 $R^{11a}$;

$C_6$–$C_{10}$ aryl substituted with 0–3 $R^{11b}$;

$C_3$–$C_{10}$ carbocycle substituted with 0–3 $R^{11b}$; and 5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —$(CH_2)_p$—;

p is 1 or 2;

X is a bond;

phenyl substituted with 0–2 $R^{Xb}$;

$C_3$–$C_6$ carbocycle substituted with 0–2 $R^{Xb}$; or 5 to 6 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_3$ haloalkyl, $C_1$–$C_3$ haloalkoxy, and $C_1$–$C_3$ halothioalkoxy;

Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)—S(=O)$_2$—;

$R^{16}$, at each occurrence, is independently selected from H, OH, $C_1$–$C_6$ alkyl, benzyl, phenethyl, ($C_1$–$C_6$ alkyl)—C(=O)—, and ($C_1$–$C_6$ alkyl)—S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)—C(=O)—, and ($C_1$–$C_6$ alkyl)—S(=O)$_2$—;

$R^{19}$, at each occurrence, is independently selected from H, OH, methyl, ethyl, propyl, butyl, phenyl, benzyl, and phenethyl;

$R^{19b}$, at each occurrence, is independently is H or $C_1$–$C_4$ alkyl;

$R^{20}$ is C(=O)$OR^{17}$;

$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

provided when Q is —$(CR^7R^{7a})_n$—$N(R^{7b})$—$R^4$ and $R^{7b}$ is ($C_1$–$C_4$ alkyl)OC(=O)—, then n is 1 or 2; and provided when Q is —$(CR^7R^{7a})_n$—$N(R^{7b})$—$R^4$ and n is 0, then $R^4$ does not contain a —C(=O)— adjacent to —$N(R^{7b})$—.

[3] In a more preferred embodiment the present invention provides for a compound of Formula (Ia):

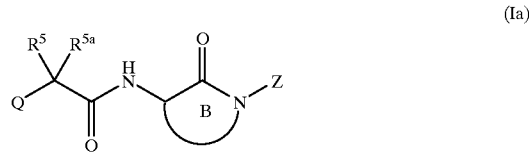

(Ia)

or a stereoisomer, pharmaceutically acceptable salt or prodrug thereof, wherein:

Q is

—$(CHR^{7a})_m$—$R^4$,

—$(CHR^{7a})_m$—CH(OH)—$R^4$,

—$(CHR^{7a})_m$—NHC(=O)—$R^4$,

—$(CHR^{7a})_n$—S—$R^4$,

—$(CHR^{7a})_n$—O—$R^4$, or

—$(CHR^{7a})_n$—N($R^{7b}$)—$R^4$;

m is 1 or 2;

n is 0 or 1;

$R^4$ is H, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{4b}$, $C_6$–$C_{10}$ aryl substituted with 0–3 $R^{4b}$, or 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, OH, F, Cl, Br, I, $CF_3$, methyl, ethyl, $C_3$–$C_{10}$ carbocycle substituted with 0–3 $R^{4b}$, $C_6$–$C_{10}$ aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $N_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ and $R^{5a}$ are combined to form a 3–8 membered carbocyclic moiety;

wherein said 3–8 membered carbocyclic moiety is saturated or partially unsaturated;

wherein said 3–8 membered carbocyclic moiety may optionally contain a heteroatom selected from —O—, —NH—, and —N($R^{20}$)—; and wherein said 3–8 membered carbocyclic moiety is substituted with 0–4 $R^{5b}$;

additionally, two $R^{5b}$ substituents on adjacent atoms may be combined to form a benzo fused radical; wherein said benzo fused radical is substituted with 0–4 $R^{23}$;

additionally, two $R^{5b}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^{5b}$ substituents on the same or adjacent carbon atoms may be combined to form a $C_3$–$C_6$ carbocycle substituted with 0–3 $R^{23}$;

$R^{5b}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, phenyl, and a 5 to 6 membered heterocycle containing 1 to 4 heteroatoms selected from nitrogen, oxygen, and sulphur;

$R^{7a}$, at each occurrence, is independently H, methyl, or ethyl;

$R^{7b}$ is H, methyl, ethyl, $CH_3OC(=O)$—, or $CH_3CH_2OC(=O)$—;

Ring B is selected from:

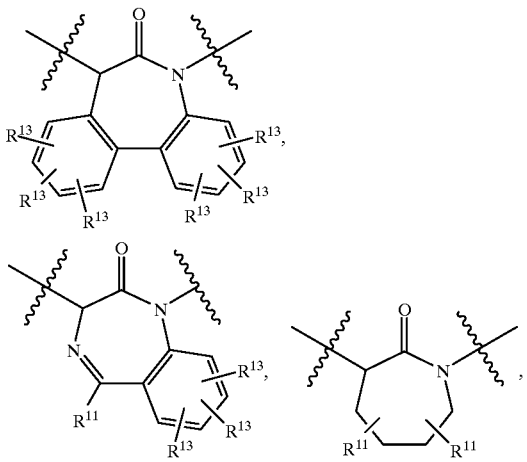

and

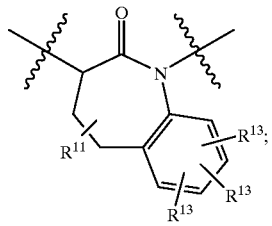

$R^{11}$, at each occurrence, is independently selected from H, $C_1$–$C_4$ alkoxy, Cl, F, Br, I, =O, CN, $N_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1$–$C_6$ alkyl optionally substituted with 0–3 $R^{11a}$;

$C_6$–$C_{10}$ aryl substituted with 0–3 $R^{11b}$;

$C_3$–$C_{10}$ carbocycle substituted with 0–3 $R^{11b}$; and 5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$ at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)—$C(=O)$—, and ($C_1$–$C_6$ alkyl)—$S(=O)_2$—;

$R^{16}$, at each occurrence, is independently selected from H, OH, $C_1$–$C_6$ alkyl, benzyl, phenethyl, ($C_1$–$C_6$ alkyl)—$C(=O)$—, and ($C_1$–$C_6$ alkyl)—$S(=O)_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{7a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)—$C(=O)$—, and ($C_1$–$C_6$ alkyl)—$S(=O)_2$—;

$R^{19}$, at each occurrence, is independently selected from H, OH, methyl, ethyl, propyl, butyl, phenyl, benzyl, and phenethyl;

$R^{23}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

provided when Q is —$(CHR^{7a})_n$—$N(R^{7b})$—$R^4$ and $R^{7b}$ is ($C_1-C_4$ alkyl)OC(=O)—, then n is 1 or 2; and provided when Q is —$(CHR^{7a})_n$—$N(R^{7b})$—$R^4$ and n is 0, then $R^4$ does not contain a —C(=O)— adjacent to —$N(R^{7b})$—.

[4] In a further more preferred embodiment the present invention provides for a compound of Formula (Ia) or a stereoisomer, pharmaceutically acceptable salt or prodrug thereof, wherein:

Q is
—$(CH_2)_m$—$R^4$,
—$(CH_2)_m$—CH(OH)—$R^4$,
—$(CH_2)_m$—NHC(=O)—$R^4$,
—$(CH_2)_n$—S—$R^4$,
—$(CH_2)_n$—O—$R^4$, or
—$(CH_2)_n$——$N(R^{7b})$—$R^4$;

m is 1 or 2;
n is 0 or 1;
$R^4$ is
$C_1-C_8$ alkyl substituted with 0–3 $R^{4a}$,
$C_2-C_8$ alkenyl substituted with 0–3 $R^{4a}$,
$C_2-C_8$ alkynyl substituted with 0–3 $R^{4a}$,
$C_3-C_{10}$ carbocycle substituted with 0–3 $R^{4b}$,
$C_6-C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, OH, F, Cl, Br, I, $CF_3$, methyl,
$C_3-C_{10}$ carbocycle substituted with 0–3 $R^{4b}$,
$C_6-C_{10}$ aryl substituted with 0–3 $R^{4b}$, and
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1-C_6$ alkyl, $C_1-C_4$ alkoxy, $C_1-C_4$ haloalkyl,
$C_1-C_4$ haloalkoxy, and $C_1-C_4$ haloalkyl-S—;

$R^5$ and $R^{5a}$ are combined to form a 3–8 membered carbocyclic moiety;
wherein said 3–8 membered carbocyclic moiety is saturated or partially unsaturated;
wherein said 3–8 membered carbocyclic moiety may optionally contain a heteroatom selected from —O—, —NH—, and —$N(R^{20})$—; and
wherein said 3–8 membered carbocyclic moiety is substituted with 0–3 $R^{5b}$;

$R^{5b}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1-C_4$ alkyl, $C_2-C_4$ alkenyl, $C_2-C_4$ alkynyl, $C_1-C_4$ alkoxy, $C_1-C_4$ haloalkyl, $C_1-C_4$ haloalkoxy, and $C_1-C_4$ haloalkyl-S—;

$R^{7b}$ is H, methyl, ethyl, $CH_3OC(=O)$—, or $CH_3CH_2OC(=O)$—;

Ring B is selected from:

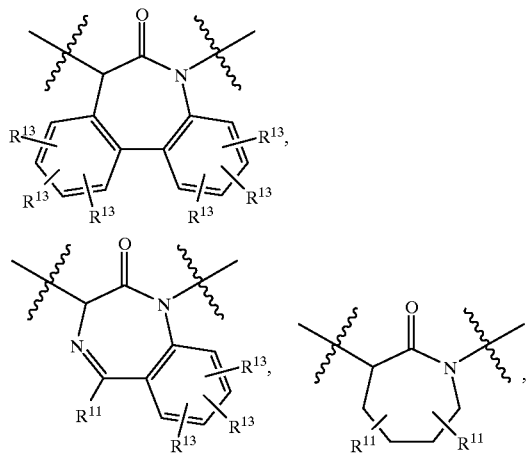

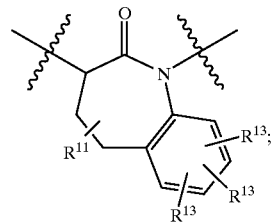

and $R^{11}$, at each occurrence, is independently selected from H, =O, $NR^{18}R^{19}$, $CF_3$;
$C_1-C_4$ alkyl optionally substituted with 0–1 $R^{11a}$; phenyl substituted with 0–3 $R^{11b}$;
$C_3-C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_{10}-C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1-C_2$ haloalkyl, and $C_1-C_2$ haloalkoxy;

W is a bond;
X is a bond;
Y is a bond;
Z is H;
$C_1-C_8$ alkyl substituted with 0–3 $R^{12a}$;
$C_2-C_6$ alkenyl substituted with 0–3 $R^{12a}$; or
$C_2-C_6$ alkynyl substituted with 0–3 $R^{12a}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—,
$C_6-C_{10}$ aryl substituted with 0–4 $R^{12b}$;
$C_3-C_{10}$ carbocycle substituted with 0–4 $R^{12b}$; and
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)—C(=O)—, and ($C_1$–$C_4$ alkyl)—S(=O)$_2$—;

$R^{16}$, at each occurrence, is independently selected from H, OH, $C_1$–$C_6$ alkyl, benzyl, phenethyl, ($C_1$–$C_4$ alkyl)—C(=O)—, and ($C_1$–$C_4$ alkyl)—S(=O)$_2$—;

$R^{18}$, at each occurrence, is independently selected from H, $C_1$–$C_6$ alkyl, phenyl, benzyl, phenethyl, ($C_1$–$C_6$ alkyl)—C(=O)—, and ($C_1$–$C_6$ alkyl)—S(=O)$_2$—;

$R^{19}$, at each occurrence, is independently selected from H, OH, methyl, ethyl, propyl, butyl, phenyl, benzyl, and phenethyl;

provided when Q is —(CH$_2$)$_n$—N(R$^{7b}$)—R$^4$ and R$^{7b}$ is ($C_1$–$C_4$ alkyl)OC(=O)—, then n is 1 or 2; and provided when Q is —(CH$_2$)$_n$—N(R$^{7b}$)—R$^4$ and n is 0, then R$^4$ does not contain a —C(=O)— adjacent to —N(R$^{7b}$)—.

[5] In a further more preferred embodiment the present invention provides:

Q is —CH$_2$R$^4$, —CH$_2$CH$_2$R$^4$, —CH$_2$CH(OH)—R$^4$, —CH$_2$NH-R$^4$, —CH$_2$CH$_2$NHR$^4$, —CH$_2$N(R$^{7b}$)—R$^4$, —CH$_2$NHC(=O)—R$^4$, or —NH—R$^4$;

R$^4$ is $C_1$–$C_6$ alkyl substituted with 0–3 R$^{4a}$, $C_2$–$C_6$ alkenyl substituted with 0–3 R$^{4a}$, $C_2$–$C_6$ alkynyl substituted with 0–3 R$^{4a}$, $C_3$–$C_6$ carbocycle substituted with 0–3 R$^{4b}$, phenyl substituted with 0–3 R$^{4b}$, or 5 to 6 membered heterocycle containing 1 to 3 heteroatoms selected from nitrogen, oxygen, and sulphur, wherein said 5 to 6 membered heterocycle is substituted with 0–3 R$^{4b}$;

R$^{4a}$, at each occurrence, is independently selected from H, OH, F, Cl, Br, I, CF$_3$, methyl, $C_3$–$C_6$ carbocycle substituted with 0–3 R$^{4b}$, phenyl substituted with 0–3 R$^{4b}$, and 5 to 6 membered heterocycle containing 1 to 3 heteroatoms selected from nitrogen, oxygen, and sulphur, wherein said 5 to 6 membered heterocycle is substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

R$^5$ and R$^{5a}$ are combined to form a 3–6 membered carbocyclic moiety;

wherein said 3–6 membered carbocyclic moiety is saturated or partially unsaturated;

wherein said 3–6 membered carbocyclic moiety may optionally contain a heteroatom selected from —O—, —NH—, and —N(R$^{20}$)—; and wherein said 3–6 membered carbocyclic moiety is substituted with 0–2 R$^{5b}$;

R$^{5b}$, at each occurrence, is independently selected from H, OH, Cl, F, Br, I, CN, NO$_2$, CF$_3$, acetyl, SCH$_3$, methyl, ethyl, methoxy, ethoxy, allyl, —OCF$_3$, and —SCF$_3$;

R$^{7b}$ is H, methyl, ethyl, CH$_3$C(=O)—, or CH$_3$CH$_2$OC(=O)—;

Ring B is selected from:

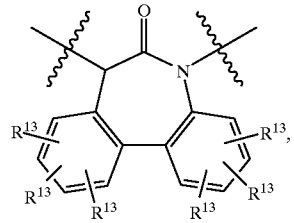

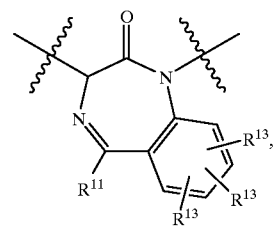 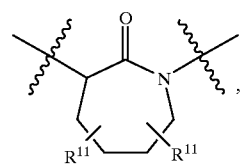

and

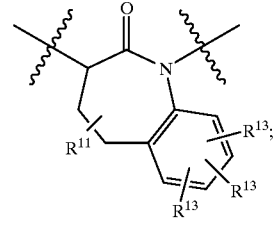

R$^{11}$, at each occurrence, is independently selected from H, =O, NR$^{18}$R$^{19}$, CF$_3$;

$C_1$–$C_4$ alkyl optionally substituted with 0–1 R$^{11a}$;

phenyl substituted with 0–3 R$^{11b}$;

$C_3$–$C_6$ carbocycle substituted with 0–3 R$^{11b}$; and 5 to 6 membered heterocycle containing 1 to 4 heteroatoms selected from nitrogen, oxygen, and sulphur, wherein said 5 to 6 membered heterocycle is substituted with 0–3 R$^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

R$^{11a}$, at each occurrence, is independently selected from H, methyl, ethyl, propyl, butyl, methoxy, ethoxy, propoxy, phenoxy, F, Cl, =O, NR$^{15}$NR$^{16}$, CF$_3$, or phenyl substituted with 0–3 R$^{11b}$;

R$^{11b}$, at each occurrence, is independently selected from H,

OH, Cl, F, NR$^{15}$R$^{16}$, CF$_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
C$_1$–C$_4$ alkyl substituted with 0–3 R$^{12a}$;
C$_2$–C$_4$ alkenyl substituted with 0–3 R$^{12a}$; or
C$_2$–C$_4$ alkynyl substituted with 0–3 R$^{12a}$;
R$^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;
R$^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;
R$^{15}$, at each occurrence, is independently selected from H, C$_1$–C$_4$ alkyl, and benzyl;
R$^{16}$, at each occurrence, is independently selected from H, OH, methyl, ethyl, propyl, butyl, benzyl, phenethyl, methyl-C(=O)—13, ethyl-C(=O)—, methyl-S(=O)$_2$—, and ethyl-S(=O)$_2$—;
R$^{18}$, at each occurrence, is independently selected from H, methyl, ethyl, propyl, butyl, phenyl, benzyl, and phenethyl;
R$^{19}$, at each occurrence, is independently selected from H, methyl, ethyl, propyl, and butyl; and
provided when Q is —NH—R$^4$, then R$^4$ does not contain a —C(=O)— adjacent to —N(R$^{7b}$)—.

[6] In a further more preferred embodiment the present invention provides:
Q is —CH$_2$R$^4$, —CH$_2$CH$_2$R$^4$, —CH$_2$CH(OH)—R$^4$, —CH$_2$NH—R$^4$, —CH$_2$CH$_2$NHR$^4$, —CH$_2$N(R$^{7b}$)—R$^4$, —CH$_2$NHC(=O)—R$^4$, or —NH—R$^4$;
R$^4$ is
C$_1$–C$_6$ alkyl substituted with 0–3 R$^{4a}$,
C$_2$–C$_6$ alkenyl substituted with 0–3 R$^{4a}$,
C$_2$–C$_6$ alkynyl substituted with 0–3 R$^{4a}$,
C$_3$–C$_6$ carbocycle substituted with 0–3 R$^{4b}$, or
phenyl substituted with 0–3 R$^{4b}$;
R$^{4a}$, at each occurrence, is independently selected from H, OH, F, Cl, Br, I, CF$_3$, methyl,
C$_3$–C$_6$ carbocycle substituted with 0–3 R$^{4b}$,
phenyl substituted with 0–3 R$^{4b}$, and
5 to 6 membered heterocycle containing 1 to 3 heteroatoms selected from nitrogen, oxygen, and sulphur, wherein said 5 to 6 membered heterocycle is substituted with 0–3 R$^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;
R$^5$ and R$^{5a}$ are combined to form a 3–6 membered carbocyclic moiety selected from cyclopropyl, cyclobutyl, cyclopentyl, cyclohexyl, and perhydro-2H-pyran; wherein said 3–6 membered carbocyclic moiety is substituted with 0–1 R$^{b\,5b}$;
R$^{5b}$ is selected from H, OH, Cl, F, CN, CF$_3$, methyl, ethyl, methoxy, ethoxy, allyl, and —OCF$_3$;
R$^{7b}$ is H, methyl, ethyl, CH$_3$OC(=O)—, or CH$_3$CH$_2$OC(=O)—;

Ring B is selected from:

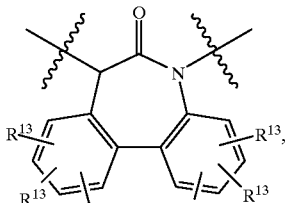

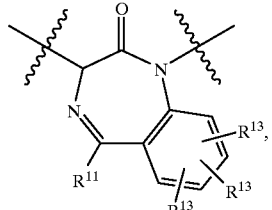

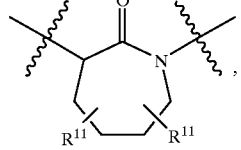

and

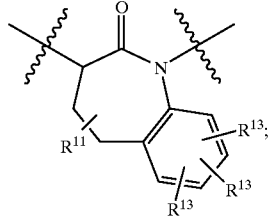

R$^{11}$, at each occurrence, is independently selected from H, =O, NR$^{18}$R$^{19}$;
C$_1$–C$_4$ alkyl optionally substituted with 0–1 R$^{11a}$;
phenyl substituted with 0–3 R$^{11b}$;
5 to 6 membered heterocycle containing 1 to 4 heteroatoms selected from nitrogen, oxygen, and sulphur, wherein said 5 to 6 membered heterocycle is substituted with 0–3 R$^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
R$^{11a}$, at each occurrence, is independently selected from H, methyl, ethyl, propyl, methoxy, ethoxy, propoxy, phenoxy, F, Cl, =O, NR$^{15}$R$^{16}$, CF$_3$, or phenyl substituted with 0–3 R$^{11b}$;
R$^{11b}$, at each occurrence, is independently selected from H, OH, Cl, F, NR$^{15}$R$^{16}$, CF$_3$, methyl, ethyl, propyl, butyl, methoxy, ethoxy, propoxy, C$_1$–C$_2$ haloalkyl, and C$_1$–C$_2$ haloalkoxy;
W is a bond;
X is a bond;
Y is a bond;
Z is H;
C$_1$–C$_4$ alkyl substituted with 0–1 R$^{12a}$;
C$_2$–C$_4$ alkenyl substituted with 0–1 R$^{12a}$;
C$_2$–C$_4$ alkynyl substituted with 0–1 R$^{12a}$;
R$^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;
R$^{13}$, at each occurrence, is independently selected from H, OH, methyl, ethyl, propyl, butyl, methoxy, ethoxy, Cl, F, Br, CN, NR$^{15}$R$^{16}$, and CF$_3$;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

provided when Q is —NH—$R^4$, then $R^4$ does not contain a

—C(=O)— adjacent to —N($R^{7b}$)—.

[7] In a further more preferred embodiment the present invention provides:

$R^5$ and $R^{5a}$ are combined to form cyclopentyl or cyclohexyl;

Q is

—CH$_2$CH$_3$,
—CH$_2$CH$_2$CH$_3$,
—CH$_2$CH$_2$CH$_2$CH$_3$,
—CH$_2$CH$_2$CH$_2$CH$_2$CH$_3$,
—CH$_2$CH$_2$CH$_2$CH$_2$CH$_2$CH$_3$,
—CH$_2$CH(CH$_3$)$_2$,
—CH$_2$CH$_2$CH(CH$_3$)$_2$,
—CH$_2$CH$_2$CH$_2$CH(CH$_3$)$_2$,
—CH$_2$CH$_2$CH$_2$CH$_2$CH(CH$_3$)$_2$,
—CH$_2$NHCH$_2$CH$_3$,
—CH$_2$NHCH$_2$CH$_2$CH$_3$,
—CH$_2$NHCH$_2$CH$_2$CH$_2$CH$_3$,
—CH$_2$NHCH(CH$_3$)$_2$,
—CH$_2$NHCH$_2$CH(CH$_3$)$_2$,
—CH$_2$NHCH$_2$CH$_2$CH(CH$_3$)$_2$,
—CH$_2$CH(OH)CH$_2$CH$_3$,
—CH$_2$CH(OH)CH$_2$CH$_2$CH$_3$,
—CH$_2$CH(OH)CH$_2$CH$_2$CH$_2$CH$_3$,
—CH$_2$CH(OH)CH(CH$_3$)$_2$,
—CH$_2$CH(OH)CH$_2$CH(CH$_3$)$_2$,
—CH$_2$CH(OH)CH$_2$CH$_2$CH(CH$_3$)$_2$,
—CH$_2$CH(cyclopropyl),
—CH$_2$CH$_2$CH(cyclopropyl),
—CH$_2$CH$_2$CH$_2$CH(cyclopropyl),
—CH$_2$N(C(=O)OCH$_2$CH$_3$)CH$_2$CH$_2$CH(CH$_3$)$_2$,
—CH$_2$NHC(=O)—CH$_2$—(3,5-diF-phenyl),
—CH$_2$NHC(=O)CH(OH)CH(CH$_3$)$_2$,
—CH$_2$NHC(=O)CH(OH)CH$_2$CH(CH$_3$)$_2$,
—CH$_2$NHC(=O)CH(OH)CH$_2$CH$_2$CH$_3$,
—CH$_2$NHCH$_2$CH(OH)CH$_2$CH(CH$_3$)$_2$,
—CH$_2$NHCH$_2$CH(OH)CH$_2$CH$_2$CH$_3$,
—CH$_2$NHCH$_2$CH(OH)CH$_2$CH$_2$CH$_2$CH$_3$,
—CH$_2$NHCH$_2$CH(OH)CH(CH$_3$)$_2$,
—CH$_2$NHCH$_2$CH$_2$-(cyclopropyl),
—CH$_2$NHCH$_2$CH$_2$-(cyclobutyl),
—CH$_2$NHCH$_2$CH$_2$-(cyclopentyl),
—CH$_2$NHCH$_2$CH$_2$-(cyclohexyl),
—CH$_2$NHCH$_2$-(cyclopropyl),
—CH$_2$NHCH$_2$-(cyclobutyl),
—CH$_2$NHCH$_2$-(cyclopentyl),
—CH$_2$NHCH$_2$-(cyclohexyl),
—CH$_2$NH-(cyclopropyl),
—CH$_2$NH-(cyclobutyl),
—CH$_2$NH-(cyclopentyl),
—CH$_2$NH-(cyclohexyl),
—CH$_2$NHCH$_2$CH$_2$—(3,5-diF-phenyl),
—CH$_2$NHCH$_2$—(1,4-diF-phenyl),
—CH$_2$CH$_2$NHCH$_2$CH(CH$_3$)$_2$,
—CH$_2$CH$_2$NHCH$_2$CH$_2$CH$_3$,
—CH$_2$CH$_2$NHCH$_2$CH$_2$CH$_2$CH$_3$,
—CH$_2$CH$_2$NHCH$_2$-(cyclopropyl),
—CH$_2$CH$_2$NHCH$_2$-(cyclobutpyl),
—CH$_2$CH$_2$NHCH$_2$-(cyclopentyl),
—CH$_2$CH$_2$NHCH$_2$-(cyclohexyl),
—NHCH$_2$CH(OH)CH(CH$_3$)$_2$,
—NHCH$_2$CH(OH)-(cyclopropyl),
—NHCH$_2$CH(OH)-(cyclobutyl),
—NHCH$_2$CH(OH)-(cyclopentyl),
—NHCH$_2$CH(OH)-(cyclohexyl), or
—CH$_2$NHCH$_2$CH(OH)-(phenyl);

W is a bond;
X is a bond;
Y is a bond;
Z is methyl, ethyl, i-propyl, n-propyl, n-butyl, i-butyl, s-butyl, t-butyl, or allyl;

$R^{11}$, at each occurrence, is independently selected from H, =O, methyl, ethyl, phenyl, benzyl, phenethyl, 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, pyrid-2-yl, pyrid-3-yl, or pyrid-4-yl; and $R^{13}$, at each occurrence, is independently selected from H, F, Cl, OH, —CH$_3$, —CH$_2$CH$_3$, —OCH$_3$, and —CF$_3$.

[8] In a further more preferred embodiment the present invention provides for a compound of Formula (I):
wherein:
Q is
—(CH$_2$)$_m$—$R^4$,
—(CH$_2$)$_m$—CH(OH)—$R^4$,
—(CH$_2$)$_m$—NHC(=O)—$R^4$,
—(CH$_2$)$_n$—S—$R^4$,
—(CH$_2$)$_n$—O—$R^4$, or
—(CH$_2$)$_n$—N($R^{7b}$)—$R^4$;
m is 1 or 2;
n is 0 or 1;
$R^4$ is
$C_1$–$C_8$ alkyl substituted with 0–3 $R^{4a}$,
$C_2$–$C_8$ alkenyl substituted with 0–3 $R^{4a}$,
$C_2$–$C_8$ alkynyl substituted with 0–3 $R^{4a}$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, OH, F, Cl, Br, I, CF$_3$, methyl,
$C_3$–$C_{10}$ carbocycle substituted with 0–3 $R^{4b}$,
$C_6$–$C_{10}$ aryl substituted with 0–3 $R^{4b}$, and 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ and $R^{5a}$ are combined to form a 3–8 membered carbocyclic moiety;

wherein said 3–8 membered carbocyclic moiety is saturated or partially unsaturated;

wherein said 3–8 membered carbocyclic moiety may optionally contain a heteroatom selected from —O—, —NH—, and —N($R^{20}$)—; and wherein said 3–8 membered carbocyclic moiety is substituted with 0–3 $R^{5b}$;

$R^{5b}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_4$ alkenyl, $C_2$–$C_4$ alkynyl, $C_1$–$C_4$ alkoxy, $C_1$–$C_4$ haloalkyl, $C_1$–$C_4$ haloalkoxy, and $C_1$–$C_4$ haloalkyl-S—;

$R^{7b}$ is H, methyl, ethyl, $CH_3OC(=O)$—, or $CH_3CH_2OC(=O)$—;

Ring B is selected from:

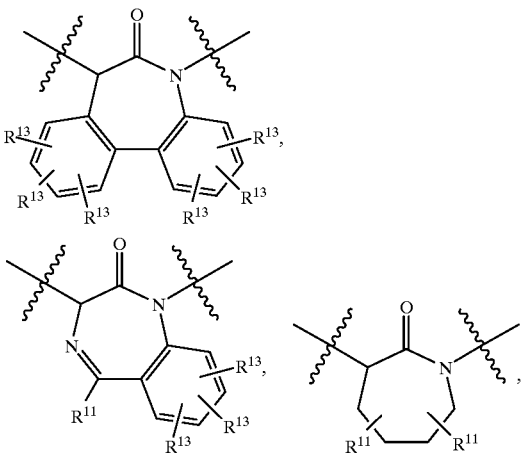

and

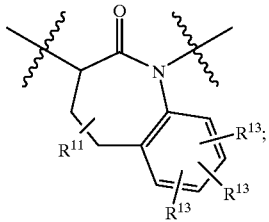

$R^{11}$, at each occurrence, is independently selected from H, =O, $NR^{18}R^{19}$, $CF_3$;

$C_1$–$C_4$ alkyl optionally substituted with 0–1 $R^{11a}$;

phenyl substituted with 0–3 $R^{11b}$;

$C_3$–$C_6$ carbocycle substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, and phenyl substituted with 0–3 $R^{11b}$;

$R^{11b}$, at each occurrence, is independently selected from H,

OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond, —$CH_2$—, —$CH_2CH_2$—;

X is a bond;

phenyl substituted with 0–2 $R^{Xb}$;

$C_3$–$C_6$ cycloalkyl substituted with 0–2 $R^{Xb}$; or 5 to 6 membered heterocycle substituted with 0–2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Y is a bond, —C(=O)—, —O—, —S—, —S(=O)—, —S(=O)$_2$—, —N($R^9$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

Z is $C_1$–$C_3$ alkyl substituted with 1–2 $R^{12a}$;

$C_6$–$C_{10}$ aryl substituted with 0–4 $R^{12b}$;

$C_3$–$C_{10}$ carbocycle substituted with 0–3 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$;

$C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)—C(=O)—, and ($C_1$–$C_4$ alkyl)—S(=O)$_2$—;

$R^{16}$, at each occurrence, is independently selected from H, OH, $C_1$–$C_6$ alkyl, benzyl, phenethyl, ($C_1$–$C_4$ alkyl)—C(=O)—, and ($C_1$–$C_4$ alkyl)—S(=O)$_2$—;

$R^{18}$, at each occurrence, is independently selected from H, $C_1$–$C_6$ alkyl, phenyl, benzyl, phenethyl, ($C_1$–$C_6$ alkyl)—C(=O)—, and ($C_1$–$C_6$ alkyl)—S(=O)$_2$—;

$R^{19}$, at each occurrence, is independently selected from H, OH, methyl, ethyl, propyl, butyl, phenyl, benzyl, and phenethyl;

$R^{9b}$, at each occurrence, is independently selected from H, methyl, ethyl, propyl, butyl, phenyl, benzyl, and phenethyl;

provided when Q is —(CH₂)ₙ—N(R⁷ᵇ)—R⁴ and R⁷ᵇ is (C₁–C₄ alkyl)OC(=O)—, then n is 1 or 2; and provided when Q is —(CH₂)ₙ—N(R⁷ᵇ)—R⁴ and n is 0, then R⁴ does not contain a —C(=O)— adjacent to —N(R⁷ᵇ)—.

[9] In a further more preferred embodiment the present invention provides:

Q is —CH₂R⁴, —CH₂CH₂R⁴, —CH₂CH(OH)—R⁴, —CH₂NH—R⁴, —CH₂CH₂NHR⁴, —CH₂N(R⁷ᵇ)—R⁴, —CH₂NHC(=O)—R⁴, or —NH—R⁴;

R⁴ is

C₁–C₆ alkyl substituted with 0–3 R⁴ᵃ,

C₂–C₆ alkenyl substituted with 0–3 R⁴ᵃ,

C₂–C₆ alkynyl substituted with 0–3 R⁴ᵃ,

C₃–C₆ carbocycle substituted with 0–3 R⁴ᵇ, phenyl substituted with 0–3 R⁴ᵇ, or 5 to 6 membered heterocycle containing 1 to 3 heteroatoms selected from nitrogen, oxygen, and sulphur, wherein said 5 to 6 membered heterocycle is substituted with 0–3 R⁴ᵇ;

R⁴ᵃ, at each occurrence, is independently selected from H, OH, F, Cl, Br, I, CF₃, methyl, C₃–C₆ carbocycle substituted with 0–3 R⁴ᵇ, phenyl substituted with 0–3 R⁴ᵇ, and 5 to 6 membered heterocycle containing 1 to 3 heteroatoms selected from nitrogen, oxygen, and sulphur, wherein said 5 to 6 membered heterocycle is substituted with 0–3 R⁴ᵇ;

R⁴ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, and C₁–C₄ haloalkyl-S—;

R⁵ and R⁵ᵃ are combined to form a 3–6 membered carbocyclic moiety;

wherein said 3–6 membered carbocyclic moiety is saturated or partially unsaturated;

wherein said 3–6 membered carbocyclic moiety may optionally contain a heteroatom selected from —O—, —NH—, and —N(R²⁰)—; and wherein said 3–6 membered carbocyclic moiety is substituted with 0–2 R⁵ᵇ;

R⁵ᵇ, at each occurrence, is independently selected from H, OH, Cl, F, Br, I, CN, NO₂, CF₃, acetyl, SCH₃, methyl, ethyl, methoxy, ethoxy, allyl, —OCF₃, and —SCF₃;

R⁷ᵇ is H, methyl, ethyl, CH₃OC(=O)—, or CH₃CH₂OC(=O)—;

Ring B is selected from:

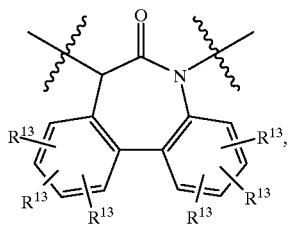

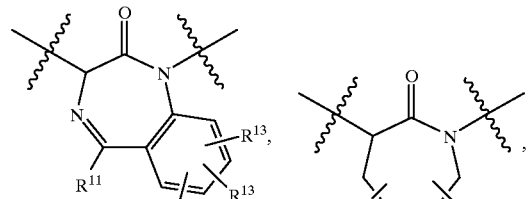

and

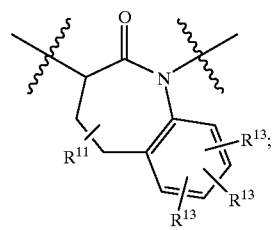

R¹¹, at each occurrence, is independently selected from H, =O, NR¹⁸R¹⁹, CF₃;

C₁–C₄ alkyl optionally substituted with 0–1 R¹¹ᵃ;

phenyl substituted with 0–3 R¹¹ᵇ;

C₃–C₆ carbocycle substituted with 0–3 R¹¹ᵇ; and 5 to 6 membered heterocycle containing 1 to 4 heteroatoms selected from nitrogen, oxygen, and sulphur, wherein said 5 to 6 membered heterocycle is substituted with 0–3 R¹¹ᵇ; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

R¹¹ᵃ, at each occurrence, is independently selected from H, methyl, ethyl, propyl, butyl, methoxy, ethoxy, propoxy, phenoxy, F, Cl, =O, NR¹⁵R¹⁶, CF₃, or phenyl substituted with 0–3 R¹¹ᵇ;

R¹¹ᵇ, at each occurrence, is independently selected from H, OH, Cl, F, NR¹⁵R¹⁶, CF₃, methyl, ethyl, propyl, butyl, methoxy, ethoxy, propoxy, C₁–C₂ haloalkyl, and C₁–C₂ haloalkoxy;

W is a bond, —CH₂—, —CH₂CH₂—;

X is a bond;

phenyl substituted with 0–1 Rˣᵇ;

C₃–C₆ cycloalkyl substituted with 0–1 Rˣᵇ; or 5 to 6 membered heterocycle substituted with 0–1 Rˣᵇ;

Rˣᵇ is selected from H, OH, Cl, F, NR¹⁵R¹⁶, CF₃, acetyl, SCH₃, S(=O)CH₃, S(=O)₂CH₃, methyl, ethyl, propyl, methoxy, ethoxy, propoxy, and —OCF₃;

Y is a bond, —C(=O)—, —O—, —S—, —S(=O)—, —S(=O)₂—, —NH—, —N(CH₃)—, or —N(CH₂CH₃)—;

Z is C₁–C₂ alkyl substituted with 1–2 R¹²ᵃ;

C₆–C₁₀ aryl substituted with 0–4 R¹²ᵇ;

C₃–C₁₀ carbocycle substituted with 0–3 R¹²ᵇ; or 5 to 10 membered heterocycle containing 1 to 4 heteroatoms selected from nitrogen, oxygen, and sulphur, wherein said 5 to 10 membered heterocycle is substituted with 0–3 R¹²ᵇ;

R¹²ᵃ, at each occurrence, is independently selected from C₆–C₁₀ aryl substituted with 0–4 R¹²ᵇ;

C₃–C₁₀ carbocycle substituted with 0–4 R¹²ᵇ; and 5 to 10 membered heterocycle containing 1 to 4 heteroatoms selected from nitrogen, oxygen, and sulphur, wherein said 5 to 10 membered heterocycle is substituted with 0–3 R¹²ᵇ;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-$C(=O)$—, ethyl-$C(=O)$—, methyl-$S(=O)_2$—, and ethyl-$S(=O)_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and provided when Q is —$(CH_2)_n$—$N(R^{7b})$—$R^4$ and $R^{7b}$ is $(C_1$–$C_4$ alkyl)OC$(=O)$—, then n is 1 or 2; and provided when Q is —$(CH_2)_n$—$N(R^{7b})$—$R^4$ and n is 0, then $R^4$ does not contain a —$C(=O)$— adjacent to —$N(R^{7b})$—.

[10] In a further more preferred embodiment the present invention provides:

Q is —$CH_2R^4$, —$CH_2CH_2R^4$, —$CH_2CH(OH)$—$R^4$, —$CH_2NH$—$R^4$, —$CH_2CH_2NHR^4$, —$CH_2N(R^{7b})$—$R^4$, —$CH_2NHC(=O)$—$R^4$, or —NH—$R^4$;

$R^4$ is $C_1$–$C_6$ alkyl substituted with 0–3 $R^{4a}$, $C_2$–$C_6$ alkenyl substituted with 0–3 $R^{4a}$, $C_2$–$C_6$ alkynyl substituted with 0–3 $R^{4a}$, $C_3$–$C_6$ carbocycle substituted with 0–3 $R^{4b}$, or phenyl substituted with 0–3 $R^{4b}$;

$R^{4a}$, at each occurrence, is independently selected from H, OH, F, Cl, Br, I, $CF_3$, methyl, $C_3$–$C_6$ carbocycle substituted with 0–3 $R^{4b}$, phenyl substituted with 0–3 $R^{4b}$, and 5 to 6 membered heterocycle containing 1 to 3 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ and $R^{5a}$ are combined to form a 3–6 membered carbocyclic moiety selected from cyclopropyl, cyclobutyl, cyclopentyl, cyclohexyl, and perhydro-2H-pyran; wherein said 3–6 membered carbocyclic moiety is substituted with 0–1 $R^{5b}$;

$R^{5b}$ is selected from H, OH, Cl, F, CN, $CF_3$, methyl, ethyl, methoxy, ethoxy, allyl, and —$OCF_3$;

$R^{7b}$ is H, methyl, ethyl, $CH_3OC(=O)$—, or $CH_3CH_2OC(=O)$—;

Ring B is selected from:

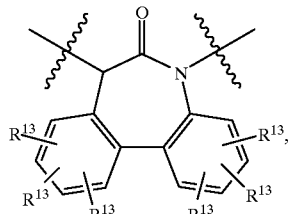

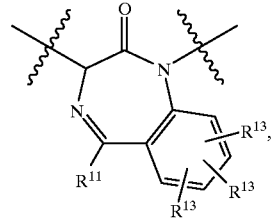

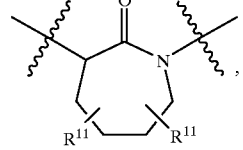

and

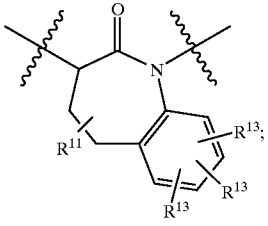

$R^{11}$, at each occurrence, is independently selected from H, =O, $NR^{18}R^{19}$;

$C_1$–$C_4$ alkyl optionally substituted with 0–1 $R^{11a}$;

phenyl substituted with 0–3 $R^{11b}$;

5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H,

OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond or —$CH_2$—;

X is a bond;

phenyl substituted with 0–1 $R^{Xb}$;

$C_3$–$C_6$ cycloalkyl substituted with 0–1 $R^{Xb}$; or 5 to 6 membered heterocycle substituted with 0–1 $R^{Xb}$;

$R^{Xb}$ is selected from H, OH, Cl, F, $NR^{15}R^{16}$, $CF_3$, acetyl, methyl, ethyl, methoxy, ethoxy, and —$OCF_3$;

Y is a bond, —$C(=O)$—, —O—, —S—, —$S(=O)$—, —$S(=O)_2$—, —NH—, —$N(CH_3)$—, or —$N(CH_2CH_3)$—;

Z is $C_1$–$C_2$ alkyl substituted with 1–2 $R^{12a}$;

$C_6$–$C_{10}$ aryl substituted with 0–4 $R^{12b}$;

$C_3$–$C_{10}$ carbocycle substituted with 0–3 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$);

$C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and —$OCF_3$;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and provided when Q is —NH—$R^4$, then $R^4$ does not contain a —C(=O)— adjacent to —N($R^{7b}$)—.

[11] In a further more preferred embodiment the present invention provides:

$R^5$ and $R^{5a}$ are combined to form cyclopentyl or cyclohexyl;

Q is
—$CH_2CH_3$,
—$CH_2CH_2CH_3$,
—$CH_2CH_2CH_2CH_3$,
—$CH_2CH_2CH_2CH_2CH_3$,
—$CH_2CH_2CH_2CH_2CH_2CH_3$,
—$CH_2CH(CH_3)_2$,
—$CH_2CH_2CH(CH_3)_2$,
—$CH_2CH_2CH_2CH(CH_3)_2$,
—$CH_2CH_2CH_2CH_2CH(CH_3)_2$,
—$CH_2NHCH_2CH_3$,
—$CH_2NHCH_2CH_2CH_3$,
—$CH_2NHCH_2CH_2CH_2CH_3$,
—$CH_2NHCH(CH_3)_2$,
—$CH_2NHCH_2CH(CH_3)_2$,
—$CH_2NHCH_2CH_2CH(CH_3)_2$,
—$CH_2CH(OH)CH_2CH_3$,
—$CH_2CH(OH)CH_2CH_2CH_3$,
—$CH_2CH(OH)CH_2CH_2CH_2CH_3$,
—$CH_2CH(OH)CH(CH_3)_2$,
—$CH_2CH(OH)CH_2CH(CH_3)_2$,
—$CH_2CH(OH)CH_2CH_2CH(CH_3)_2$,
—$CH_2CH(cyclopropyl)$,
—$CH_2CH_2CH(cyclopropyl)$,
—$CH_2CH_2CH_2CH$ (cyclopropyl),
—$CH_2N(C(=O)OCH_2CH_3)CH_2CH_2CH(CH_3)_2$,
—$CH_2NHC(=O)$—$CH_2$-(3,5-diF-phenyl),
—$CH_2NHC(=O)CH(OH)CH(CH_3)_2$,
—$CH_2NHC(=O)CH(OH)CH_2CH(CH_3)_2$,
—$CH_2NHC(=O)CH(OH)CH_2CH_2CH_3$,
—$CH_2NHCH_2CH(OH)CH_2CH(CH_3)_2$,
—$CH_2NHCH_2CH(OH)CH_2CH_2CH_3$,
—$CH_2NHCH_2CH(OH)CH_2CH_2CH_2CH_3$,
—$CH_2NHCH_2CH(OH)CH(CH_3)_2$,
—$CH_2NHCH_2CH_2$-(cyclopropyl),
—$CH_2NHCH_2CH_2$-(cyclobutyl),
—$CH_2NHCH_2CH_2$-(cyclopentyl),
—$CH_2NHCH_2CH_2$-(cyclohexyl),
—$CH_2NHCH_2$-(cyclopropyl),
—$CH_2NHCH_2$-(cyclobutyl),
—$CH_2NHCH_2$-(cyclopentyl),
—$CH_2NHCH_2$-(cyclohexyl),
—$CH_2NH$-(cyclopropyl),
—$CH_2NH$-(cyclobutyl),
—$CH_2NH$-(cyclopentyl),
—$CH_2NH$-(cyclohexyl),
—$CH_2NHCH_2CH_2$—(3,5-diF-phenyl),
—$CH_2NHCH_2$—(1,4-diF-phenyl),
—$CH_2CH_2NHCH_2CH(CH_3)_2$,
—$CH_2CH_2NHCH_2CH_2CH_3$,
—$CH_2CH_2NHCH_2CH_2CH_2CH_3$,
—$CH_2CH_2NHCH_2$-(cyclopropyl),
—$CH_2CH_2NHCH_2$-(cyclobutpyl),
—$CH_2CH_2NHCH_2$-(cyclopentyl),
—$CH_2CH_2NHCH_2$-(cyclohexyl),
—$NHCH_2CH(OH)CH(CH_3)_2$,
—$NHCH_2CH(OH)$-(cyclopropyl),
—$NHCH_2CH(OH)$-(cyclobutyl),
—$NHCH_2CH(OH)$-(cyclopentyl),
—$NHCH_2CH(OH)$-(cyclohexyl), or
—$CH_2NHCH_2CH(OH)$-(phenyl);

W is a bond or —$CH_2$—;

X is a bond;

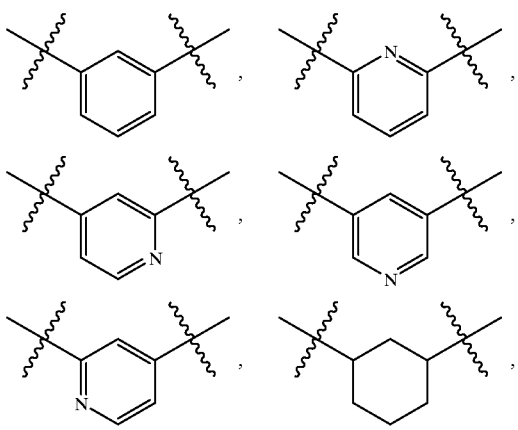

-continued or

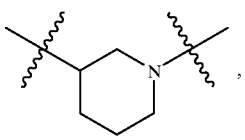

Y is a bond, —C(=O)—, —O—, —S—, —S(=O)—, —S(=O)₂—, —NH—, or —N(CH₃)—,

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—,(thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-pipridinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-pipridinyl)CH₂CH₂—;

$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4—CH₃-phenyl, (4—CH₃-phenyl)CH₂—, (4—CH₃-phenyl)CH₂CH₂—, 3—CH₃-phenyl, (3—CH₃-phenyl)CH₂—, (3—CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, or pyrid-4-yl; and $R^{13}$, at each occurrence, is independently selected from H, F, Cl, OH, —CH₃, —CH₂CH₃, —OCH₃, and —CF₃.

[12] In a further more preferred embodiment the present invention provides for a compound of Formula (Ic):

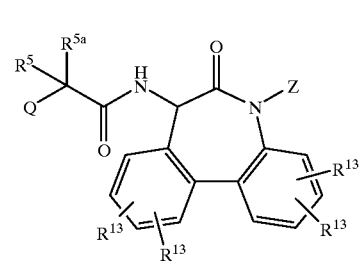

(Ic)

or a stereoisomer, pharmaceutically acceptable salt or prodrug thereof.

[13] In a further more preferred embodiment the present invention provides for a compound of Formula (Id):

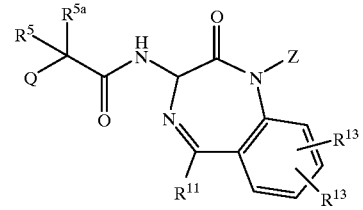

or a stereoisomer, pharmaceutically acceptable salt or prodrug thereof.

[14] In a further more preferred embodiment the present invention provides for a compound of Formula (Ie):

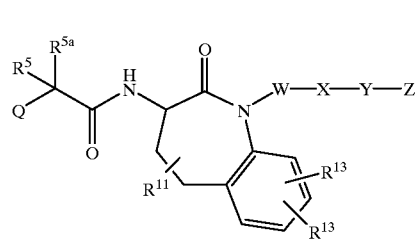

(Ie)

or a stereoisomer, pharmaceutically acceptable salt or prodrug thereof.

[15] In a further more preferred embodiment the present invention provides for a compound of Formula (Ie):

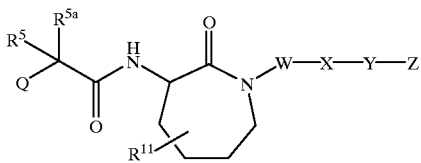

(If)

or a stereoisomer, pharmaceutically acceptable salt or prodrug thereof.

[16] In a further even more preferred embodiment the present invention provides for a compound selected from:

1-{[(3-methylbutyl)amino]methyl}-N-[6,7-dihydro-5-methyl-6-oxo-5H-dibenzo[b,d]azepin-7-yl]-cyclopentanecarbocyclic amide;

1{[N'-(ethoxycarbonyl)-N'-(3-methylbutyl)amino]methyl}-N-[6,7-dihydro-5-methyl-6-oxo-5H-dibenzo[b,d]azepin-7-yl]-cyclopentanecarbocyclic amide;

4-{[(3-methylbutyl)amino]methyl}-4-{N-[6,7-dihydro-5-methyl-6-oxo-5H-dibenzo[b,d]azepin-7-yl]carbamoyl}-perhydro-2H-pyran;

1-(2-hydroxy-pentyl)-N-[6,7-dihydro-5-methyl-6-oxo-5H-dibenzo[b,d]azepin-7-yl]-cyclopentanecarbocyclic amide;

4-{[[(3,5-difluorophenyl)methyl]amido]methyl}-4-{N-[6,7-dihydro-5-methyl-6-oxo-5H-dibenzo[b,d]azepin-7-yl]carbamoyl}-perhydro-2H-pyran;

2-(S)-hydroxy-3-methyl-N-({[N-(5-methyl-6-oxo (7H-dibenzo [d,f]azaperhydroepin-7-yl))carbamoyl]cyclopentyl}methyl)butanamide;

2-(S)-hydroxy-4-methyl-N-({[N-(5-methyl-6-oxo(7H-dibenzo[d,f]azaperhydroepin-7-yl))carbamoyl]cyclopentyl}methyl)pentanamide;

2-(3,5-difluorophenyl)-N-({[N-(5-methyl-6-oxo(7H-dibenzo[d,f]azaperhydroepin-7-yl))carbamoyl]cyclopentyl}methyl)acetamide;

N-(5-methyl-6-oxo(7H-dibenzo[d,f]azaperhydroepin-7-yl))({2-[(2-methylpropyl)amino]ethyl}cyclopentyl)carboxamide;

({2-[(cyclopropylmethyl)amino]ethyl}cyclopentyl)-N-(5-methyl-6-oxo(7H-dibenzo[d,f]azaperhydroepin-7-yl))carboxamide;

[({[2-(3,5-difluorophenyl)ethyl]amino}methyl)cyclopentyl]-N-(5-methyl-6-oxo(7H-dibenzo[d,f]azaperhydroepin-7-yl))carboxamide;

[({[(1,4-difluorophenyl)methyl]amino}methyl)cyclopentyl]-N-(5-methyl-6-oxo(7H-dibenzo[d,f]azaperhydroepin-7-yl))carboxamide;

({[(2-cyclopentylethyl)amino]methyl}cyclopentyl)-N-(5-methyl-6-oxo(7H-dibenzo[d,f]azaperhydroepin-7-yl))carboxamide;

{[((2S)-2-hydroxy-4-methylpentyl)amino]cyclopentyl}-N-(5-methyl-6-oxo(7H-dibenzo[d,f]azaperhydroepin-7-yl))carboxamide;

{[((2S)-2-hydroxy-3-methylbutyl)amino]cyclopentyl}-N-(5-methyl-6-oxo(7H-dibenzo[d,f]azaperhydroepin-7-yl))carboxamide;

{[((2S)-2-cyclohexyl-2-hydroxyethyl)amino]cyclopentyl}-N-(5-methyl-6-oxo(7H-dibenzo[d,f]azaperhydroepin-7-yl))carboxamide;

1-{[(3-methylbutylamino]methyl}-N-{(S)-1,3-dihydro-1-methyl-2-oxo-5-[4-(trifluoromethyl)phenyl]-2H-1,4-benzodiazepin-3-yl}-cyclopentanecarbocylic amide;

1-(5-methyl)hexyl-N-{(S)-1,3-dihydro-1-methyl-2-oxo-5-phenyl-2H-1,4-benzodiazepin-3-yl}-cyclopentanecarbocylic amide;

1-pentyl-N-{(S)-1,3-dihydro-1-methyl-2-oxo-5-phenyl-2H-1,4-benzodiazepin-3-yl}-cyclopentanecarbocylic amide;

1-(2-hydroxypentyl)-N-{(S)-1,3-dihydro-1-methyl-2-oxo-5-phenyl-2H-1,4-benzodiazepin-3-yl}-cyclopentanecarbocylic amide;

2-(S)-hydroxy-3-methyl-N-{[(N-{1 -methyl-2-oxo-5-[4-(trifluoromethyl)phenyl](3H-benzo[f]1,4-diazepin-3-yl)}carbamoyl)cyclopentyl]methyl}butanamide;

(2S)-N-({[N-(7-fluoro-1-methyl-2-oxo-5-phenyl(3H-benzo[f]1,4-diazepin-3-yl))carbamoyl]cyclopentyl}methyl)-2-hydroxy-3-methylbutanamide;

(2S)-N-({[N-(5-cyclopentyl-1-methyl-2-oxo(3H-benzo[f]1,4-diazepin-3-yl))carbamoyl]cyclopentyl}methyl)-2-hydroxy-3-methylbutanamide;

{[(cyclohexylamino)methyl]cyclopentyl}-N-(5-methyl-6-oxo(7H-dibenzo[d,f]azaperhydroepin-7-yl))carboxamide;

({[(2-hydroxyhexyl)amino]methyl}cyclopentyl)-N-{1-methyl-2-oxo-5-[4-(trifluoromethyl)phenyl](3H-benzo[f]1,4-diazepin-3-yl)}carboxamide;

({[((2R)-2-hydroxy-2-phenylethyl)amino]methyl}cyclopentyl)-N-{1-methyl-2-oxo-5-[4-(trifluoromethyl)phenyl](3H-benzo[f]1,4-diazepin-3-yl)}carboxamide; and ({[((2S)-2-hydroxy-2-phenylethyl)amino]methyl}cyclopentyl)-N-{1-methyl-2-oxo-5-[4-(trifluoromethyl)phenyl](3H-benzo[f]1,4-diazepin-3-yl)}carboxamide.

It is understood that any and all embodiments of the present invention may be taken in conjunction with any other embodiment to describe additional even more preferred embodiments of the present invention.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

```
1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e. =O), then 2 hydrogens on the atom are replaced.

When any variable (e.g. $R^{5b}$) occurs more than one time in any constituent or formula for a compound, its definition at each occurrence is independent of its definition at every other occurrence. Thus, for example, if a group is shown to be substituted with 0–2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon—carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon—carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, "carbocyclic moiety" is intended to mean any stable 3- to 8-membered monocyclic ring of carbon atoms, any of which may be saturated or partially unsaturated. Additionally, the 3 to 8 membered monocyclic ring of carbon atoms may be contain a heteroatom selected from oxygen, sulphur, or nitrogen, wherein a carbon atom of the ring has been substituted for the heteroatom. Examples of such carbocycles include, but are not limited to, cyclopropyl, cyclobutyl, cyclopentyl, cyclohexyl, cycloheptyl, cyclooctyl, cyclopent-3-enyl, cyclohex-3-enyl, tetrahydrofurnayl, pyranyl, pyrrolidinyl, and piperidinyl. Preferred examples of a "carbocyclic moiety" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, or $C_1$–$C_4$ haloalkyl.

As used herein, the term "heteroaryl fused radical" is intended to denote a 5 or 6 membered aromatic ring comprising carbon atoms and one or two heteroatoms selected from nitrogen, sulphur and oxygen. The 5 or 6 membered ring is fused to two adjacent atoms of a second ring, i.e. a bicyclic ring system, wherein the second ring is a "carbocyclic moiety" as defined above. Examples of a "heteroaryl fused radical" are furanyl, imidazolyl, isoxazolyl, oxazolyl, pyrrolyl, thiophenyl, thiazolyl, isothiozalyl, pyridyl, pyridazinyl, pyrimidinyl, and pyrazinyl.

The phrase "additional lactam carbons", as used herein, is intended to denote the number of optional carbon atoms in the lactam ring B of Formula (I). Formula (I"):

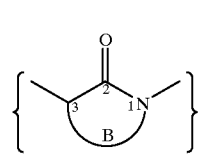

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. It is further understood that lactam ring B may optionally be unsaturated or partially unsaturated (i.e. two adjacent atoms in the ring form a double bond) wherein the backbone of lactam ring B may contain one, two or three double bonds. Examples of lactam ring B include:
B1
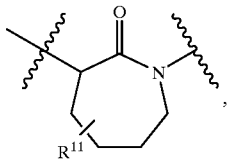
B2
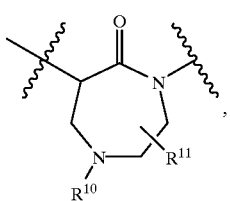
B3
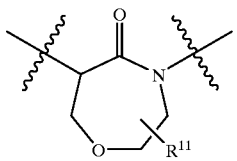
B4
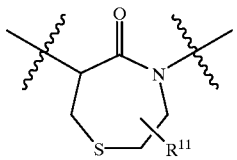
B5
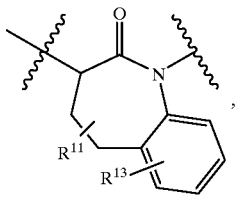
B6
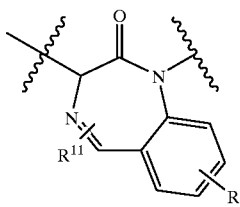
B8
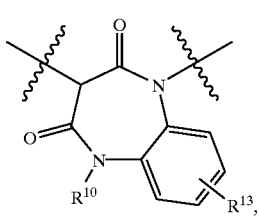
B9
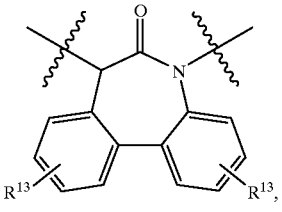
B10
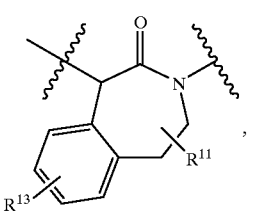
B11
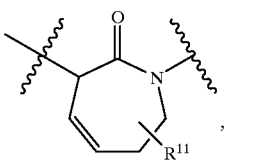
B12
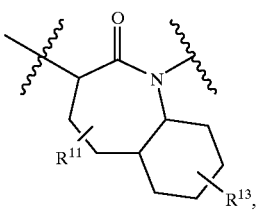
B13
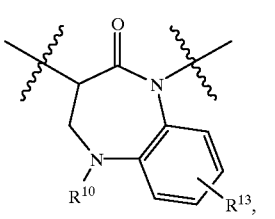
B14
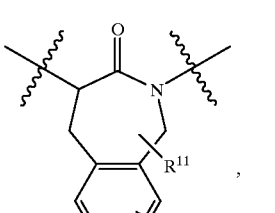
B15

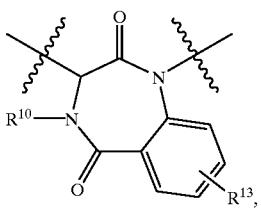
B16 but are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are hydrogen, methyl, ethyl, phenyl, benzyl, phenethyl, 4-fluorophenyl, 4-chlorophenyl, 4-methylphenyl, 4-$CF_3$-phenyl, (4-fluorophenyl)methyl, (4-chlorophenyl)methyl, (4-methylphenyl)methyl, (4-$CF_3$-phenyl)methyl, (4-fluorophenyl)ethyl, (4-chlorophenyl)ethyl, (4-methylphenyl)ethyl, (4-$CF_3$-phenyl)ethyl, and 2-, 3-, and 4-pyridinyl. More preferred examples of substituent $R^{10}$ or $R^{11}$ on lactam B are methyl, ethyl, phenyl, 4-fluorophenyl, 4-chlorophenyl, 4-$CF_3$-phenyl, (4-fluorophenyl)methyl, (4-chlorophenyl)methyl, (4-$CF_3$-phenyl)methyl, and 2-, 3-, and 4-pyridinyl. Preferred examples of $R^{13}$ on lactam B are F, Cl, OH, methyl, ethyl, methoxy, and trifluoromethyl.

It is understood that the functional group of the formula —NH—C(OH)$_2$— is equivalent to —NH—C(=O)—.

The compounds herein described may have asymmetric centers. One enantiomer of a compound of Formula (I) may display superior biological activity over the opposite enantiomer. For example carbon 3 of lactam ring B Formula (I″) may exist in either an S or R configuration. Thus, an R or S configuration at carbon 3 in Formula (I″) is considered part of the invention. An example of such configuration includes, the S isomer:

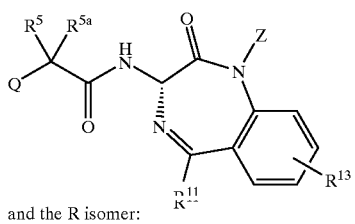

and the R isomer:

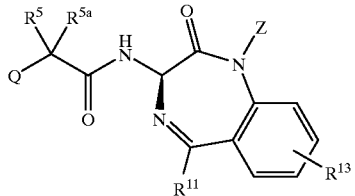

but is not intended to be limited to this example of ring B. When required, separation of the racemic material can be achieved by methods known in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section.

The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred method of synthesis, the compounds of Formula (I) of the present invention can be prepared from carboxylic acid 1 and amine 2 using amide bond syntheses known in the art, including methods commonly used in peptide syntheses, such as HATU, TBTU, BOP, EDC, CDI, and DCC-mediated couplings, as illustrated in Scheme 1. Depending on the structure of the final product, it is appreciated by those skilled in the art that protecting groups or precursor functionality convertible to the desired groups may be desirable. Protecting groups and their use in synthesis are described in Green and Wuts, *Protective Groups in Organic Synthesis,* (Wiley 1991).

Additionally, the syntheses of a representative aminomethyl carboxamide 4a, lactate 7b, and a representative homoaldol 4c of Formula (I) are illustrated in Scheme 2 and Scheme 3, respectively. As will be readily apparent to those of ordinary skill in the art, the synthetic procedures illustrated in Scheme 2 and 3, and the reaction conditions described below can be modified by selecting the appropriate starting materials and reagents to allow the preparation of other compounds of the present invention.

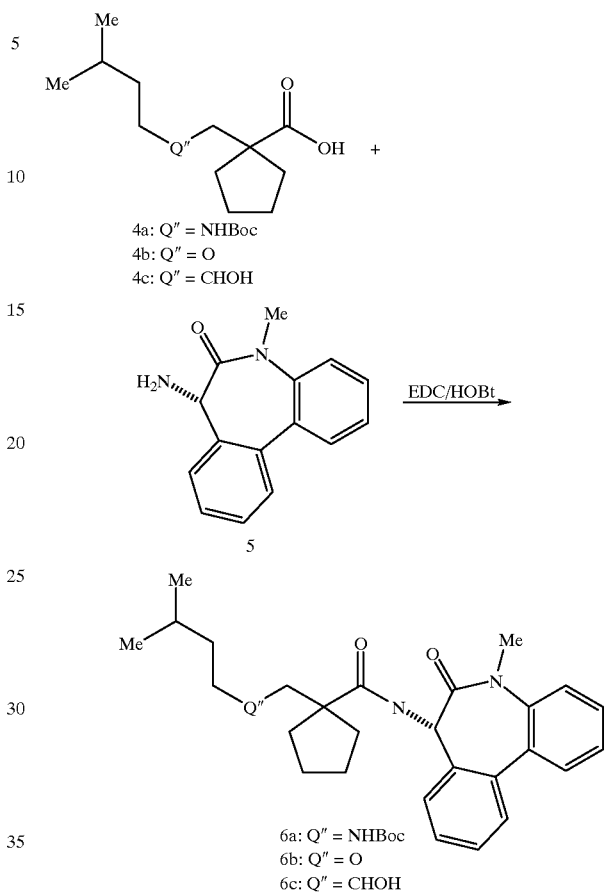

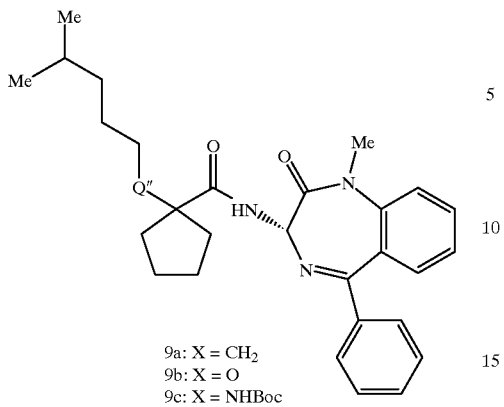

9a: X = CH$_2$
9b: X = O
9c: X = NHBoc

Methods for the synthesis of lactams useful as intermediates in the synthesis of compounds of the present invention, including amino bisbenzodiazepine 5 and amino benzodiazepine 8, are known in the art and are disclosed in a number of references including PCT publication number WO 98/28268, WO 99/66934, and WO00/07995, which are hereby incorporated by reference. Additional references include Bock, et. al., J. Org. Chem., 1987, 52, 3232–3239; Sherrill et. al., J. Org. Chem., 1995, 60, 730–734; Walsh, D. A., Synthesis, September 1980, p. 677; and Brown, at. al., Tetrahedron Letters, 1971, 8, 667–670.

Aminomethyl cyclic carboxylic acid intermediates, such as 4a, are useful for the synthesis of the current invention, and may be synthesized by a number of ways well known in the art. One of the preferred syntheses of the compound of this invention is shown in Scheme 4. Potassium carbonate-promoted double alkylation reaction of methyl ester 10 can be employed to give the cyclic ester 11. The cyanocarboxylic ester 11 is readily reduced to the corresponding amine under the reaction conditions described by Brown, R. R. et al., Synthesis, 1982, 1036. The completion of intermediate 4a can be achieved by performing the reductive amination reaction on 12 (J. Org. Chem., 1996, 61, 3849–3862), followed by the hydrolysis of ester 13. It should be apparent to those of ordinary skill in the art that many derivatives of 4a can be prepared in a similar manner from the versatile intermediate 12, upon the selection of an appropriate starting material and following procedures known in the literature.

Scheme 4

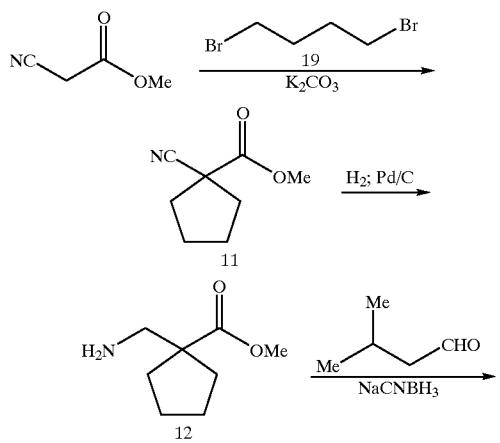

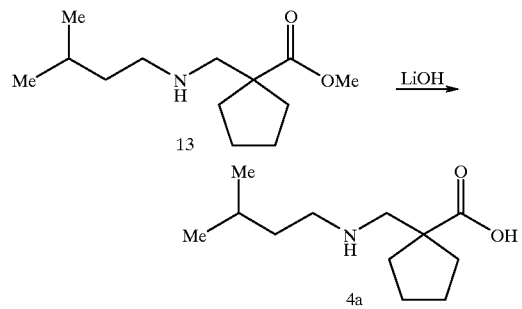

One of the representative syntheses of homoaldol analogs, such as 15, is illustrated in Scheme 5. The useful intermediate lactones, such as 14, are known in the art and one of their syntheses are described in J. Org. Chem., 1996, 61, 3849–3862.

One of the preferred syntheses of cyclic lactates, such as 7b, which are useful in the preparation of compounds of Formula (I), is outlined in Scheme 6. As illustrated for the synthesis of carboxylic acid 7b, intermediate 17 can be prepared by from ester 16, under the reaction conditions which are known in the art and disclosed in a number of references including J. Org. Chem., 1986, 51, 2402, and Chem. Rev., 1992, 92, 919. Finally, adduct 7b can be prepared by the alkylation of 17 and hydrolysis of the resulting ester.

Depending on the structure of the final product, it is appreciated by those skilled in the art, the synthetic procedure illustrated in Scheme 4, 5, and 6 and the reaction conditions described will allow the preparation of many other analogs of 4 and 7 by selecting the appropriate starting materials and reagents. Many of the starting materials employed in this invention are either commercially available or can be prepared from commercially available materials using conventional procedures and reagents.

Scheme 5

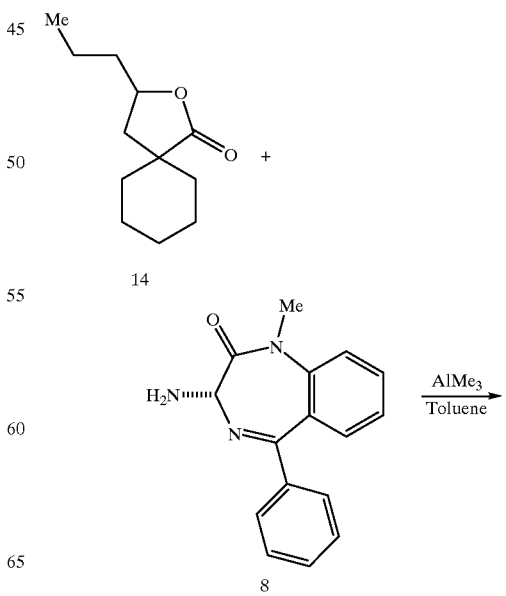

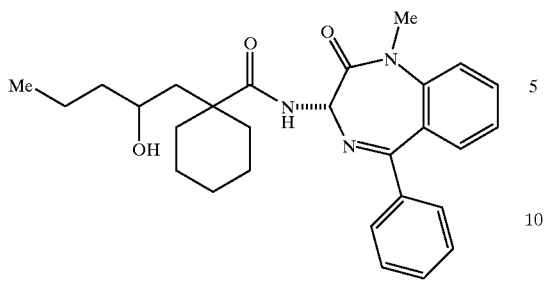

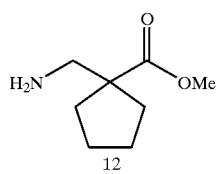

Scheme 6

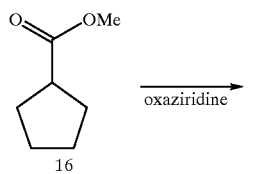

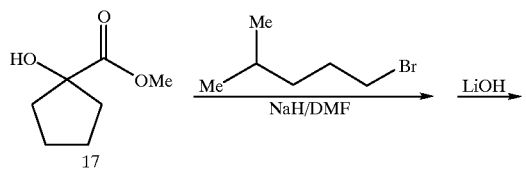

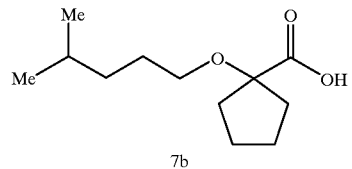

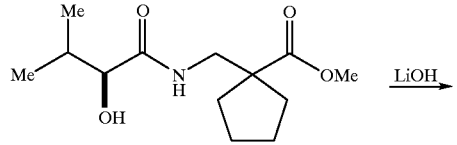

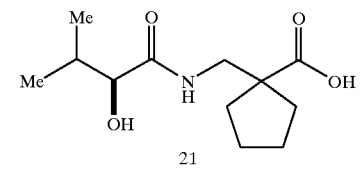

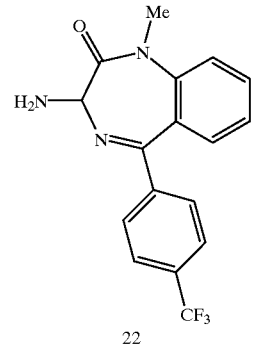

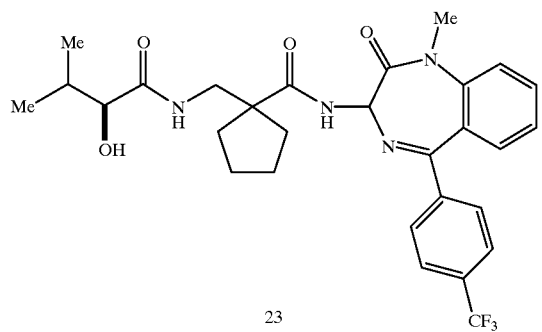

In order to assist in a further understanding of the current invention, one of the representative syntheses of the final inhibitors, such as compound 23, is illustrated in Scheme 7. Target 23 was prepared in 5 steps beginning with starting materials 10 and 18. The initial intermediate 12 was easily prepared under the reaction conditions that are know in the art (Justus Liebigs Ann. Chem. GE., 639, 1961, 166–180 and Helv. Chim. Acta. 1998, 2218–2243). EDC-promoted coupling reaction of the acid 19 and 12 provided the intermediate 20 that was subsequently hydrolyzed by LiOH and coupled with the amine 22 to give the final product 23.

Scheme 7

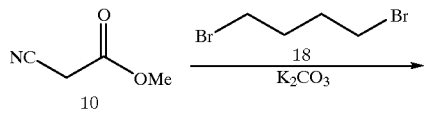

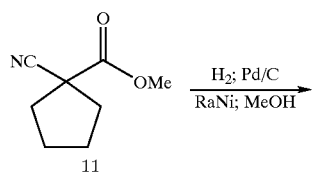

Scheme 8

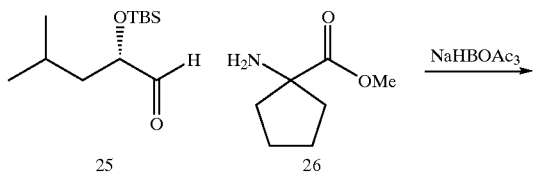

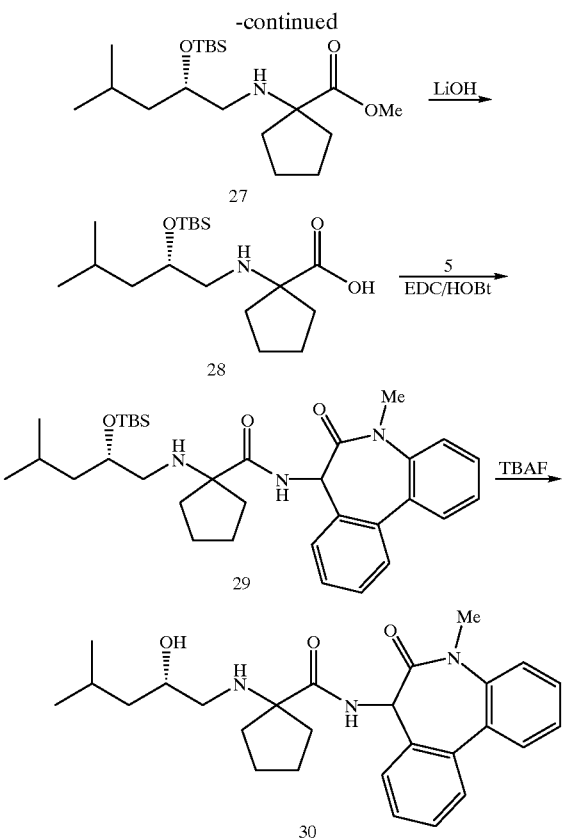

In order to assist in a further understanding of the current invention, one of the representative syntheses of the amino alcohol APP inhibitors, such as compound 30, is illustrated in Scheme 8. Molecule 30 was prepared in 5 steps. The starting aldehyde 25 was synthesized according to the published procedure of Chem. Lett 1992, 1169–1172. All other reaction conditions are known in the art. The employed reductive amination reaction was describe in J. Org. Chem., 1996, 61, 3849.

Abbreviations used in the description of the chemistry and in the examples that follow are:

| | |
|---|---|
| Ac | acetyl or acetate, |
| aq | aqueous, |
| Bn | benzyl, |
| Boc | tertiary butyloxycarbonyl, |
| BOP | benzotriazol-1-yloxytris-(dimethylamino)-phosphonium hexafluorophosphate, |
| Cbz | benzyloxycarbonyl, |
| DIEA | N,N'-diisopropylethylamine, |
| DMAP | 4-dimethylaminopyridine, |
| DMPU | 1,3-dimethyl-3,4,5,6-tetrahydro-2(1H)-pyrimidone, |
| DME | ethylene glycol dimethyl ether, |
| DMF | N,N'-dimethylformamide, |
| DMSO | dimethylsulfoxide or methyl sulfoxide, |
| EDC · HCl | 1-(3-dimethylaminopropyl)-3-ethylcarbodiimide, |
| HATU | O-(7-azabenzotriazol-1-yl)-N,N,N',N'-tetramethyluronium hexafluorophosphate, |
| HOBT | 1-hydroxybenzotriazole, |
| HPLC | high performance liquid chromatography, |
| LiHMDS | lithium hexamethyldisilazide, |
| MeCN | acetonitrile, |
| MS | mass spectrometry, |
| satd | saturated, |
| rt or RT | room temperature, |
| TBTU | O-(1H-benzotriazol-1-yl)-N,N,N',N'-tetramethyluronium hexafluorophosphate, |
| TFA | trifluoroacetic acid, |
| THF | tetrahydrofuran, and |
| TLC | thin layer chromatography. |

EXAMPLES

Compounds of the present invention are generally purified by HPLC using conditions known to one skilled in the art. However, unless otherwise indicated, the following conditions are generally applicable.

HPLC Condition A:

Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid).

HPLC Condition B:

Alternatively, reverse-phase HPLC can be carried out using a Vydac C-18 column with gradient elution from 10% to 90% acetonitrile in water.

Example 1

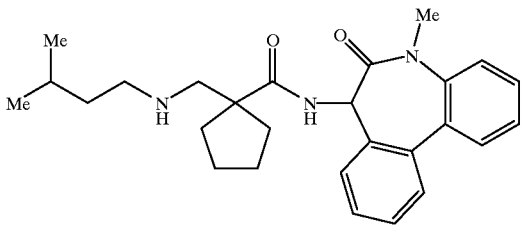

(a) ({[(3-methylbutyl)amino]methyl}cyclopentyl)methan-1-ol

To a solution of methyl 1-[N-(3-methylbutyl)-carbamoyl]-cyclopentanecarboxylate (900 mg, 3.7 mmol) in THF at rt was added $BH_3$/THF complex ) 7.4 mL, 7.4 mmol) and stirred at 75° C. for 5 hours. To this reaction mixture was added 6N HCl (10 mL) and the mixture was further stirred for 30 min before the solution was neutralized by 1N NaOH. The solution was diluted with water and extracted with EtOAc. The combined extracts were dried over magnesium sulfate, and concentrated to a crude oil (700 mg, 95%). MS $[M+H]^+200$.

(b) (tert-butoxy)-N-{[(hydroxymethyl)cyclopentyl]methyl}-N-(3-methylbutyl)carboxamide To a solution of ({[(3-methylbutyl)amino]methyl}-cyclopentyl)methan-1-ol (700 mg, 3.7 mmol) in a 1:1 mixture of $CH_2Cl_2$/MeOH (20 ml) at 0 ° C. was added $NaHCO_3$ (471 mg, 5.5 mmol) followed by $Boc_2O$ (967 mg, 4.4 mmol). The mixture was stirred at 0° C. for 30 min then warmed to rt and stirred for 1 hr. About 30 ml of $H_2O$ was added and the mixture was extracted with EtOAc (2×30 mL). The combined extracts were washed with water, dried over $MgSO_4$, filtered and concentrated to colorless oil (300mg, 68%). MS $[M+H]^+300$.

(c) 1-{[(tert-butoxy)-N-(3-methylbutyl)carbonylamino]-methyl}-cyclopentanecarboxylic Acid To a solution of (tert-butoxy)-N-{[(hydroxymethyl)-cyclopentyl]methyl}-N-(3-methylbutyl)carboxamide (300 mg, 2.5 mmol) in a 1:1:1 mixture of MeCN/H$_2$O/CCl$_4$ (30 ml) at rt was added RuCl$_3$ (10 mg, 0.05 mmol) followed by NaIO$_4$ (2.2 g, 10.25 mmol). The mixture was stirred at rt for 16 hr, then 30 ml of H$_2$was added and the mixture was extracted with CH$_2$Cl$_2$ (2×30 mL). The combined extracts were washed with water, dried over MgSO$_4$, filtered and concentrated to a crude oil (560mg, 71%). MS [M+H]$^+$314.

(d) ({[(3-methylbutyl)amino]methyl}cyclopentyl)-N-(5-methyl-6-oxo(7H-dibenzo[d,f]azepin-7-yl))carboxamide To a solution of 1-{[(tert-butoxy)-N-(3-methylbutyl)-carbonylamino]methyl}-cyclopentanecarboxylic acid (100 mg, 0.3 mmol) in CH$_2$Cl$_2$/DMF (5:1, 15 mL) at 0° C. was added HOBT (50 mg, 0.33 mmol) and EDC (63 mg, 0.33 mmol). The mixture was stirred for 10 min, then 7-amino-5-methyl-7H-dibenzoazaperhydropin-6-one (obtained as the first eluting peak of the racemic mixture on a CHIRALCEL OD column using 20% iPrOH/Hexane with diethylamine) (68 mg, 0.3 mmol) was added and stirring was continued for 1 h. The solution was poured into water and the layers separated. The aqueous layer was extracted with methylene chloride and the combined extracts were washed with water, 1 N HCl, sat'd NaHCO$_3$, dried over magnesium sulfate, and concentrated to a glassy solid which was dissolved in methylene chloride (20 mL) and TFA (6 mL) at 0° C. The mixture was stirred for 45 min., evaporated to dryness, then dissolved in Et$_2$O (20 mL). To this solution was added 1M HCl (in Et$_2$O) to form the desired HCl salt. The white solid was collected by filtration, re-dissolved in EtOAc and neutralized using 1N NaOH. The solution was diluted with water and extracted with EtOAc. The combined extracts were dried over magnesium sulfate, and concentrated to a glassy solid (45 mg, 39%). $^1$H NMR (300 MHz, CDCl$_3$) δ7.20–7.58 (m, 8H), 5.38 (d, 1H), 3.45 (s, 3H), 2.80 (s, 2H), 2.75 (m, 2H), 1.4–2.30 (m, 11H), 0.8 (d, 6H). MS [M+H]$^+$ 434.

Example 2

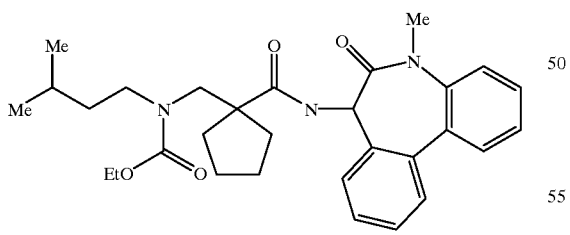

The title compound was prepared in a manner similar to that described for Example 1. The product was obtained as a colorless oil. $^1$H NMR (300 MHz, CDCl$_3$) δ7.20–7.58 (m, 8H), 5.38 (d, 1H), 4.20 (m, 2H), 3.60 (m, 2H), 3.40 (s, 3H), 3.00 (m, 1H), 1.20–2.20 (m, 14H), 0.8 (d, 6H). MS [M+H]$^+$ 506.

Example 3

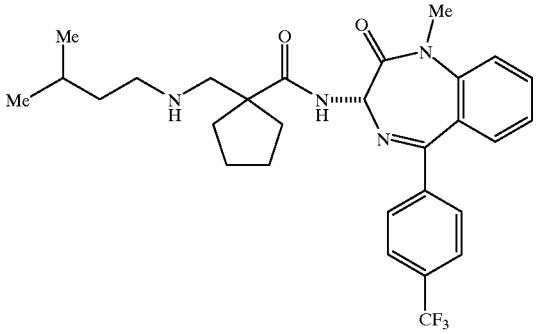

The title compound was prepared in a manner similar to that described for Example 1. This compound was made from the corresponding amino benzodiazepine that, as the Cbz protected form, was the first eluting peak of the racemic mixture on a CHIRALPAK AD column using acetonitrile. The product was obtained as a colorless oil. $^1$H NMR (300 MHz, CDCl$_3$) δ7.20–7.80 (m, 8H), 5.60 (d, 1H), 3.45 (s, 3H), 2.80 (s, 2H), 2.75 (m, 2H), 1.4–2.20 (m, 1H), 0.90 (m, 6H). MS [M+H]$^+$529.

Example 4

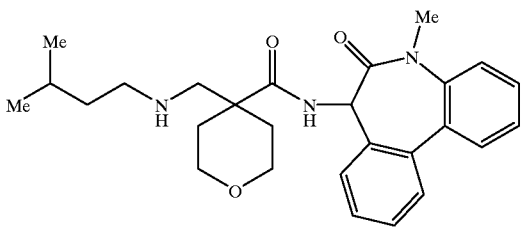

The title compound was prepared in a manner similar to that described for Example 1 using the amino bisbenzazepine employed in Example 1. The product was obtained as a colorless oil. $^1$H NMR (300 MHz, CDCl$_3$) δ6 7.64–7.32 (m, 8H), 5.41 (d, 1H), 3.88–3.70 (m, 4H), 3.36 (s, 3H), 2.88–2.75 (m, 4H), 1.80–1.48 (m, 7H), 0.94 (d, 6H). MS [M+H]$^+$450.

Example 5

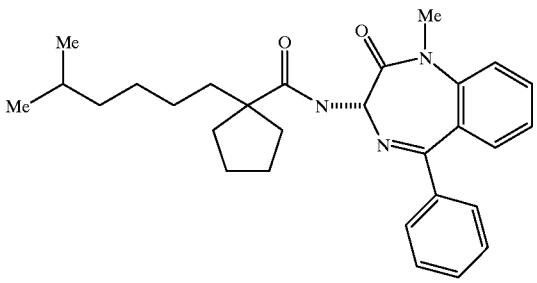

(a) Methyl 1-(5-methylhexyl)cyclopentanecarboxylate

To a solution of methyl cyclopentanecarboxylate (300 mg, 2.3 mmol) in THF (20 ml) at −78° C. was added LHMDS (4.6 mL, 4.6 mmol) and stirred for 30 min, and followed by 1-bromo-5-methylhexane (626 mg, 3.5 mmol). The mixture was stirred from −78° C. to rt over 16 hr, before 30 ml of H₂O was added and then was extracted with CH₂Cl₂ (2×30 mL). The combined extracts were washed with water, dried over MgSO₄, filtered and concentrated, then purified using flash chromatography to give an oil (110 mg, 21%). MS [M+H]⁺333.

(b) 1-(5-Methylhexyl)cyclopentanecarboxylic Acid

To a solution of methyl 1-(5-methyl-hexyl) cyclopentanecarboxylate (110 mg, 0.4 mmol) in 21 mL of THF cooled to 0° C. was added dropwise a solution of lithium hydroxide monohydrate (26 mg, 0.6 mmol) in 5.0 mL of water. The reaction mixture was stirred at rt for 16 h. THF was removed under reduced pressure to give a yellow oil which was diluted with 10 mL of 1 N HCl. The aqueous phase was extracted with CH₂Cl₂ (8×15 mL), and the extracts were combined, dried over Na₂SO₄, and concentrated to afford 60 mg (71%) of the desired product. MS [M+H]⁺213.

(c) [(5-methylhexyl)cyclopentyl]-N-(1-methyl-2-oxo-5-phenyl((S)-3H-benzo[f]1,4-diazepin-3-yl))carboxamide To a solution of 1-(5-methylhexyl)cyclopentane-carboxylic acid (20 mg, 0.09 mmol) in CH₂Cl₂/DMF (5:1, 15 mL) at 0° C. was added HOBT (15 mg, 0.1 mmol) and EDC (19 mg, 0.1 mmol). The mixture was stirred for 10 min then (S)-3-amino-1-methyl-5-phenyl-3H-benzo[f]1,4-diazepin-2-one (48 mg, 0.1 mmol) was added and stirring was continued for 1 h. The solution was poured into water and the layers separated. The aqueous layer was extracted with methylene chloride and the combined extracts were washed with water, 1N HCl, sat'd NaHCO₃, dried over magnesium sulfate, concentrated, and purified using flash chromatography to give a white solid (25 mg, 66%). ¹H NMR (300 MHz, CDCl₃) δ7.15–7.58 (m, 9H), 5.48 (d, 1H), 3.40 (s, 3H), 2.80 (m, 2H), 1.22–2.70 (m, 14H), 0.8 (d, 6H). MS [M+H]⁺460.

Example 6

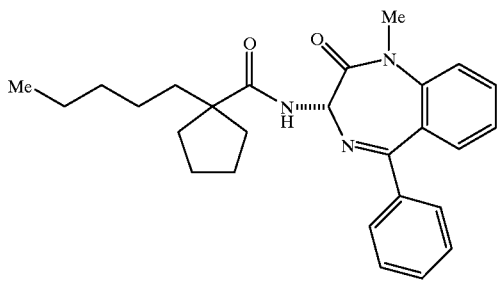

The title compound was prepared in a manner similar to that described for Example 5. The product was obtained as a colorless oil. 1H NMR (300 MHz, CDCl₃) δ7.62–7.20 (m, 9H), 5.58 (d, 1H), 3.47 (s, 3H), 2.28–2.15 (m, 2H), 1.78–1.12 (m, 14H), 0.91 (t, 3H). MS [M+H]⁺432.

Example 7

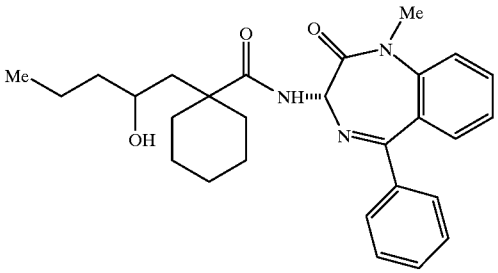

The title compound was prepared in a manner similar to the reaction described in J. Org. Chem. 1994, 59, 520 and described for Example 1. The product was obtained as a colorless oil. ¹H NMR (300 MHz, CDCl₃) δ0.90 (t, J=7 Hz, 3H), 1.25–1.70 (mbr, 15H), 1.78–1.90 (m, 1H), 2.10–2.26 (br, 2H), 3.45 (s, 3H), 3.82–3.93 (m, 1H), 5.60 (d, J=8 Hz, 1H), 7.21–7.28 (m, 1H), 7.35–7.42 (m, 4H), 7.45–7.50 (m, 1H), 7.58–7.65 (m, 3H), 7.73 (d, J=8 Hz, 1H). MS [M+H]⁺ 462.

Example 8

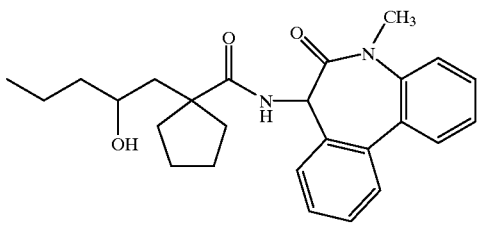

The title compound was prepared in a manner similar to that described for Example 7 from the appropriate intermediates. The product was obtained as a colorless oil. MS [M+H]⁺448.

Example 9

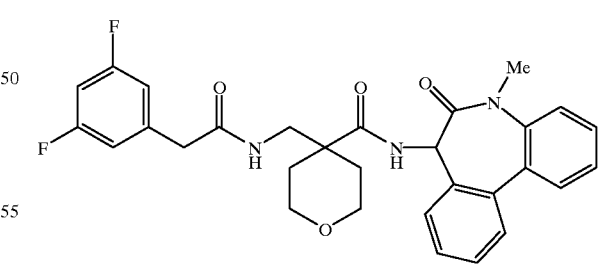

The title compound was prepared in a manner similar to that described for Example 1 using the amino bisbenzazepine employed in Example 1. The product was obtained as a colorless oil. ¹H NMR (300 MHz, CDCl₃) δ7.20–7.58 (m, 9H), 6.60–6.80 (m, 4H), 5.38 (d, 1H), 3.80–4.0 (m, 4H), 3.50 (s, 2H), 2.40 (s, 3H), 2.15 (m, 2H), 1.70 (m, 4H). MS [M+H]⁺534.

Example 10

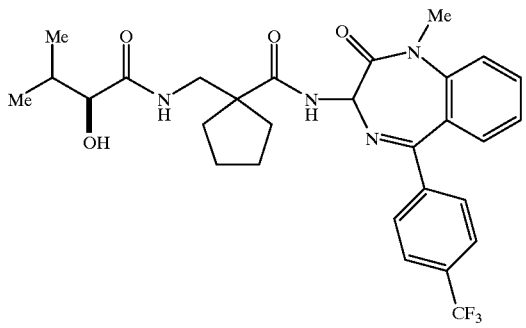

(a) methyl 1-cyanocyclopentanecarboxylate

A solution of methyl 2-cyanoacetate (30 mL, 340 mmol) in DMF (26 mL) and DBU (112 mL, 748 mmol) was heated to 50° C. for 15 min and then cooled to −20° C. To this stirred solution was added dibromobutane 18. The internal temperature increased to 70° C. during the addition. The reaction was set aside to cool to rt before quenching with $H_2O$ (800 mL). The product was extracted with $Et_2O$ (3×300 mL). The ether layer was washed with 1N HCl (400 mL) and $H_2O$ (400 mL). The combined extracts were dried over magnesium sulfate, and concentrated to a crude oil that was distilled under high vacuum at 80° C. to yield the desired product in 58% yield.

(b) methyl 1-(aminomethyl)cyclopentanecarboxylate

To a solution of methyl 1-cyanocyclopentanecarboxylate (15 g, 98 mmol) in MeOH (250 mL) was added RaNi (3 g). The reaction was charged with $H_2$ at 50 psi and shaken in the Parr shaker for 24 h. The RaNi catalyst was removed by filtration through a layer of celite. The solvent was removed under vacuum. The crude product was dissolved in 1N $NaHSO_4$ (100 mL) and then washed with $Et_2O$ (2×100 mL). The organic layer was dried over magnesium sulfate and then filtered. The solvents were removed under reduced pressure to provide the amine in 77%; $^1$H NMR (300 MHz, $CD_3OD$) δ3.75 (s, 3H), 3.12 (s, 2H), 2.14×2.07 (m, 2H), 1.83×1.65 (m, 6H). MS $[M+H]^+$470.

(c) methyl 1-[(2-(S)-hydroxy-3-methylbutanoylamino)methyl]cyclopentanecarboxylate To a solution of (S)-2-hydroxy-3-methyl-butyric acid (300 mg, 2.5 mmol) in $CH_2Cl_2$/DMF (5:1, 20 mL) at 0° C. was added HOBT (382 mg, 2.5 mmol) and EDC (477 mg, 2.5 mmol). The mixture was stirred for 10 min then methyl 1-(aminomethyl)cyclopentanecarboxylate (321 mg, 2.25 mmol) and $iPr_2NEt$ (0.5 mL, 2.5 mmol) were added and stirring was continued for 3 h. The reaction was diluted with water and extracted with EtOAc. The combined extracts were washed with water, 1N HCl, sat'd $NaHCO_3$, dried over magnesium sulfate, concentrated, and purified using flash chromatography to give a white solid (420 mg, 72%). MS $[M+H]^+$258.

(d) 1-[(2-(S)-hydroxy-3-methylbutanoylamino)methyl]-cyclopentanecarboxylic Acid

To a solution of methyl 1-[(2-(S)-hydroxy-3-methylbutanoylamino)methyl] cyclopentane carboxylate (170 mg, 0.66 mmol) in 21 mL of THF cooled to 0° C. was added dropwise a solution of lithium hydroxide monohydrate (110 mg, 2.6 mmol) in 5.0 mL of water. The reaction mixture was stirred at rt for 6 h. THF was removed under reduced pressure to give a yellow oil which was diluted with 10 mL of 1 N HCl. The aqueous phase was extracted with $CH_2Cl_2$ (2×15 mL), and the extracts were combined, dried over $Na_2SO_4$, and concentrated to afford 105 mg (65%) of the desired product. MS $[M+H]^+$244.

(e) 2-(S)-hydroxy-3-methyl-N-{[(N-{1-methyl-2-oxo-5-[4-(trifluoromethyl)phenyl] (3H-benzo[f]1,4-diazepin-3-yl)}carbamoyl) cyclopentyl]methyl} Butanamide To a solution of 1-[(2-(S)-hydroxy-3-methylbutanoylamino)methyl] cyclopentanecarboxylic acid (110 mg, 0.45 mmol) in $CH_2Cl_2$/DMF (5:1, 15 mL) at rt was added HOBT (75 mg, 0.49 mmol) and EDC (95 mg, 0.49 mmol). The mixture was stirred for 10 min then (S)-3-amino-1-methyl-5-[4-(trifluoromethyl)phenyl]-3H-benzo[f] 1,4-diazepin-2-one hydrogen bromide salt (186 mg, 0.45 mmol) and $iPr_2NEt$ (0.1 mL, 0.49 mmol) were added and stirring was continued for 16 h. (The amino benzodiazepine was obtained as described in Example 3.) The reaction was diluted with water, extracted with EtOAc and the combined extracts were washed with water, 1 N HCl, sat'd $NaHCO_3$, dried over magnesium sulfate, concentrated on the rotavapor, and purified on the flash chromatography to give a white solid (120 mg, 48%). $^1$H NMR (300 MHz, $CDCl_3$) δ7.20–7.80 (m, 8H), 6.60–6.80 (m, 4H), 5.48 (d, 1H), 4.00 (d, 1H), 3.40–3.60 (m, 2H), 3.50 (s, 3H), 1.60–2.20 (m, 9H) 1.00 (d, 3H), 0.9 (d, 3H); MS $[M+H]^+$559.

Example 11

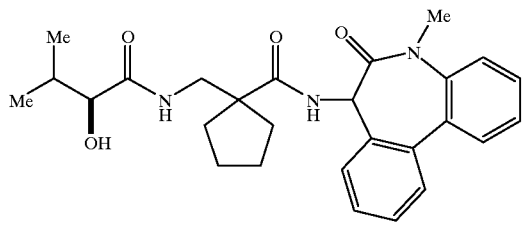

The title compound was prepared in a manner similar to that described for Example 9 using the amino bisbenzazepine employed in Example 1. The product was obtained as a colorless oil. $^1$H NMR (300 MHz, $CDCl_3$) δ7.20–7.80 (m, 8H), 6.60–6.80 (m, 4H), 5.20 (d, 1H), 3.80 (d, 1H), 3.40 (d, 2H), 3.30 (s, 3H), 1.60–2.20 (m, 9H) 1.00 (d, 3H), 0.80 (d, 3H); MS $[M+H]^+$464.

Example 12

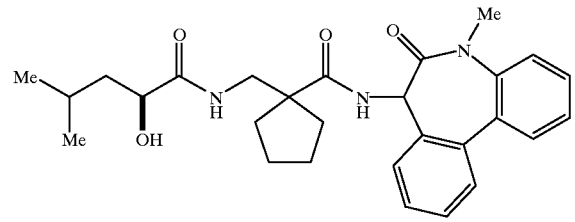

The title compound was prepared in a manner similar to that described for Example 9 using the amino bisbenzazepine employed in Example 1. The product was obtained as a colorless oil. $^1$H NMR (300 MHz, $CDCl_3$) δ7.20–7.80 (m, 8H), 5.20 (d, 1H), 4.00 (m, 1H), 3.40 (m, 2H), 3.30 (s, 3H), 1.40–2.20 (m, 11H), 0.80 (m, 6H); MS $[M+H]^+$478.

Example 13

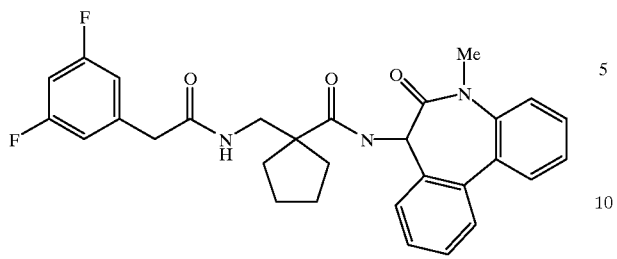

The title compound was prepared in a manner similar to that described for Example 9 using the amino bisbenzazepine employed in Example 1. The product was obtained as a colorless oil. $^1$H NMR (300 MHz, CDCl$_3$) δ7.65–7.15 (m, 9H), 6.80–6.60 (m, 4H), 5.25 (d, 1H), 3.43–3.36 (m, 7H), 2.15×1.70 (m, 8H). MS [M+H]$^+$518.

Example 14

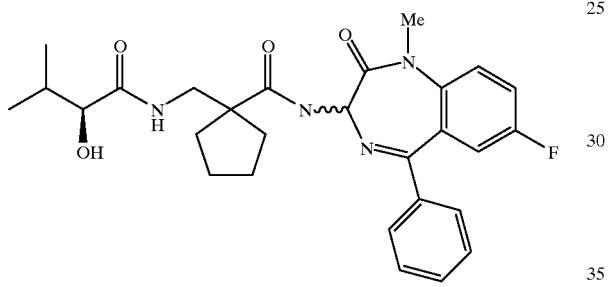

The title compound was prepared in a manner similar to that described for Example 9. The product was obtained as a colorless oil. $^1$H NMR (300 MHz, CDCl$_3$) δ7.60–7.26 (m, 9H), 7.20 (m, 1H), 7.02 (m, 1H), 5.47 (d, 1H), 3.92 (d, 1H), 3.60–3.38 (m, 5H), 2.18–1.62 (m, 9H), 0.97 (d, 3H), 0.82 (d, 3H). MS [M +H]$^+$509.

Example 15

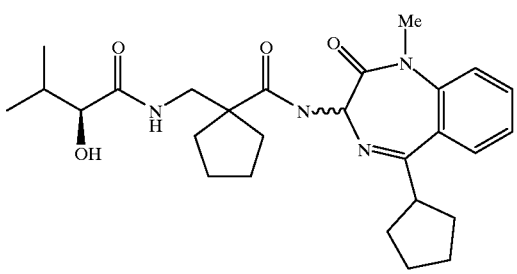

The title compound was prepared in a manner similar to that described for Example 9. The product was obtained as a colorless oil. $^1$H NMR (300 MHz, CDCl$_3$) δ7.58–7.46 (m, 2H), 7.36–7.24 (m, 2H), 5.31 (d, 1H), 3.97 (m, 1H), 3.76–3.26 (m, 6H), 2.20–1.10 (m, 17H), 1.00 (d, 3H), 0.85 (d, 3H). MS [M+H]$^+$483.

Example 16

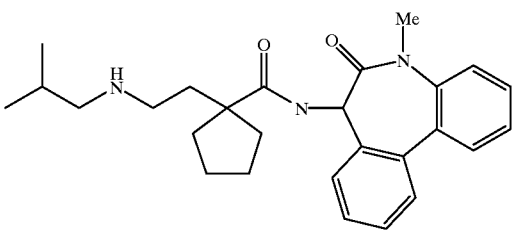

The title compound was prepared in a manner similar to that described for Example 1 using the amino bisbenzazepine employed in Example 1. The product was obtained as a colorless oil. $^1$H NMR (300 MHz, CDCl$_3$) δ7.56–7.22 (m, 8H), 5.24 (d, 1H), 3.29 (s, 3H), 2.64–1.54 (m, 15H), 0.80 (d, 6H). MS [M+H]$^+$434.

Example 17

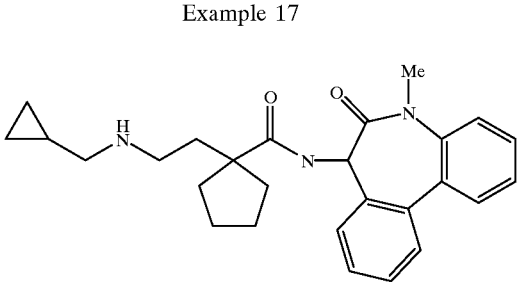

The title compound was prepared in a manner similar to that described for Example 1 using the amino bisbenzazepine employed in Example 1. The product was obtained as a colorless oil. $^1$H NMR (300 MHz, CDCl$_3$) δ7.52–7.20 (m, 8H), 5.22 (d, 1H), 3.25 (s, 3H), 2.58 (m, 2H), 2.36 (d, 2H), 2.10 (m, 2H), 1.82 (m, 2H), 1.70–1.50 (m, 6H), 0.91 (m, 1H), 0.36 (m, 2H), 0.01 (m, 2H). MS [M+H]$^+$432.

Example 18

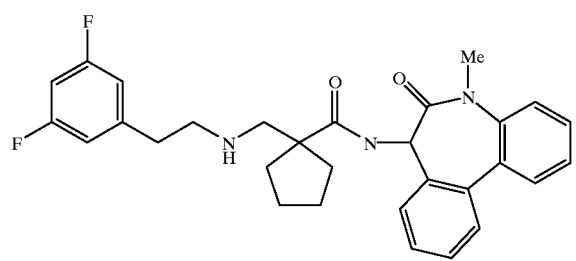

The title compound was prepared in a manner similar to that described for Example 1 using the amino bisbenzazepine employed in Example 1. $^1$H NMR (300 MHz, CDCl$_3$) δ7.61–7.28 (m, 8H), 6.83–6.61 (m, 3H), 5.37 (d, 1H), 3.36 (s, 3H), 3.06–2.88 (m, 6H), 2.20–1.42 (m, 8H). MS [M+H]$^+$504.

Example 19

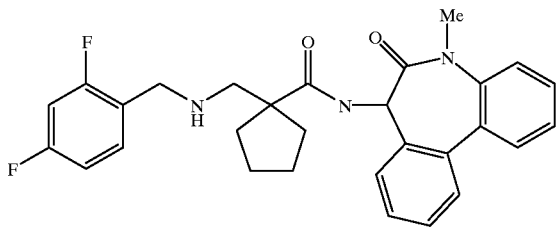

The title compound was prepared in a manner similar to that described for Example 1 using the amino bisbenzazepine employed in Example 1. The product was obtained as a colorless oil. $^1$H NMR (300 MHz, CDCl$_3$) δ7.61–7.20 (m, 8H), 7.07–7.00 (m, 2H), 6.70 (m, 1H), 5.37 (d, 1H), 3.99–3.85 (q, 2H), 3.37 (s, 3H), 2.87–2.80 (q, 2H), 2.20–1.52 (m, 8H). MS [M+H]$^+$490.

Example 20

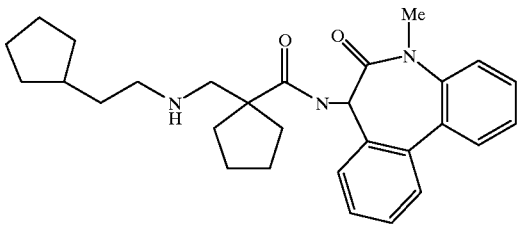

The title compound was prepared in a manner similar to that described for Example 1 using the amino bisbenzazepine employed in Example 1. The product was obtained as a colorless oil. $^1$H NMR (300 MHz, CDCl$_3$) δ7.60–7.30 (m, 8H), 5.37 (d, 1H), 3.35 (s, 3H), 2.92–2.79 (m, 4H), 2.22–1.02 (m, 19H). MS [M+H]$^+$460.

Example 21

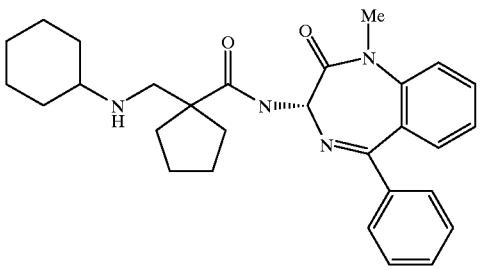

The title compound was prepared in a manner similar to that described for Example 1. The product was obtained as a white solid (173 mg, 75%): mp=82–86° C.; $^1$H NMR (500 MHz, CD$_3$OD) δ7.71 (t, J=2.3 Hz, 1H), 7.69–7.31 (m, 8H), 5.36 (s, 1H), 3.48 (s, 3H), 2.87 (m, 2H), 2.52 (m, 1H), 2.15–2.01 (m, 4H), 1.78–1.59 (m, 10H), 1.32–1.20 (m, 4H); IR (CH$_2$Cl$_2$) 2928, 2853, 2360, 1689, 1658, 1520, 1448, 698 cm$^{-1}$; ESI MS m/z=473 [C$_{29}$H$_{36}$N$_4$O$_2$+H]$^+$; HPLC>95%, t$_r$=19.92 min; Anal. Calcd. for C$_{29}$H$_{36}$N$_4$O$_2$-0.25H$_2$O; C, 72.99; H, 7.72; N, 11.75. Found: C, 72.80; H, 7.68; N, 11.47 colorless oil. MS [M+H]$^+$460.

Example 22

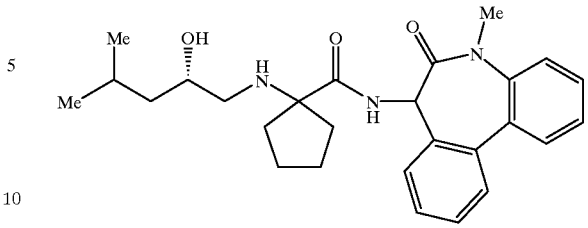

(a) 27 (Scheme 8).

To a stirred solution of aldehyde 25 (1.2 g, 5.6 mmol) in CH$_2$Cl$_2$ (20 ml) at 25° C. was added amine 26 (1 g, 5.6 mmol). After 30 min. NaHB(OAc)$_3$ (3.5 g, 16.8 mmol) was added. The mixture was stirred at rt for 16 hr, then 30 ml of H$_2$O was added and the mixture was extracted with CH$_2$Cl$_2$ (2×30 mL). The combined extracts were washed with water, dried over MgSO$_4$, filtered and concentrated, then purified using flash chromatography to give a clear oil (1 g, 53%). MS [M+H]$^+$333.

(b) 28 (Scheme 8).

To a solution of 27 (1 g, 2.8 mmol) in 21 mL of THF cooled to 0° C. was added dropwise a solution of lithium hydroxide monohydrate (588 mg, 14 mmol) in 5.0 mL of water. The reaction mixture was stirred at rt for 16 h. THF was removed under reduced pressure to give a yellow oil which was diluted with 10 mL of 1 N HCl. The aqueous phase was extracted with CH$_2$Cl$_2$ (8×15 mL), and the extracts were combined, dried over Na$_2$SO$_4$, and concentrated to afford 750 mg (78%) of the desired product. MS [M+H]$^+$213.

(c) 29 (Scheme 8).

To a solution of the acid 28 (240 mg, 0.69 mmol) in DMF (15 mL) at 0° C. was added HATU (288 mg, 0.76 mmol). The mixture was stirred for 10 min and then 7-amino-5-methyl-7H-dibenzoazaperhydropin-6-one (160 mg, 0.69 mmol) was added followed by iPrNEt$_2$ (0.14 mL, 0.76 mmol and stirring was continued for 16 h. (The amino bisbenzazepine was obtained as the first eluting peak of the racemic mixture on a CHIRALCEL OD column using 20% iPrOH/ Hexane with diethylamine). The solution was poured into water and the layers separated. The aqueous layer was extracted with EtOAc and the combined extracts were washed with water, 1N HC$_1$, sat'd NaHCO$_3$, dried over magnesium sulfate, concentrated, then purified using flash chromatography to give an oil (300 mg, 77%). MS [M+H]$^+$ 433.

(d) 30 (Scheme 8).

To a solution of 29 (300 mg, 0.53 mmol) in THF (20 ml) at 25° C. was added TBAF (2.7 mL, 2.66 mmol). The mixture was stirred at rt for 16 hr, then 30 ml of H$_2$O was added and the mixture was extracted with CH$_2$Cl$_2$ (2×30 mL). The combined extracts were washed with water, dried over MgSO$_4$, filtered and concentrated, then purified using flash chromatography to give a clear oil (150 mg, 63%). $^1$H NMR (300 MHz, CDCl$_3$) δ7.30–7.60 (m, 8H), 5.40 (d, 1H), 3.90 (m, 1H), 3.20 (s, 3H), 2.60 (m, 2H), 1.60–2.20 (m, 9H) 1.50 (m, 1H), 1.20 (m, 1H), 0.80 (m, 6H); MS [M+H]$^+$450.

Example 23

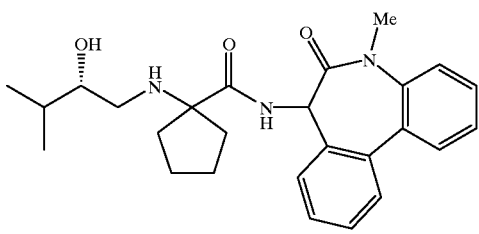

The title compound was prepared in a manner similar to that described for Example 21 using the amino bisbenzazepine employed in Example 1. The product was obtained as a colorless oil. $^1$H NMR (300 MHz, CDCl$_3$) δ7.30–7.60 (m, 8H), 5.40 (d, 1H), 3.60 (m, 1H), 3.40 (s, 3H), 2.60 (m, 2H), 1.60–2.20 (m, 11H) 1.05 (d, 3H), 0.90 (d, 3H); MS [M+H]$^+$ 436.

Example 24

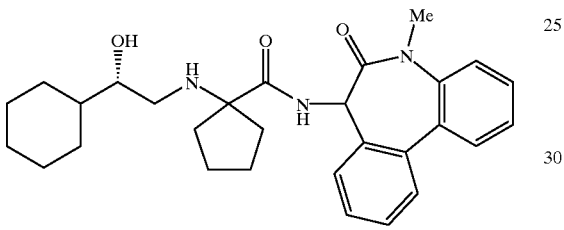

The title compound was prepared in a manner similar to that described for Example 21 using the amino bisbenzazepine employed in Example 1. The product was obtained as a colorless oil. $^1$H NMR (300 MHz, CDCl$_3$) δ7.30–7.60 (m, 8H), 5.40 (d, 1H), 3.60 (m, 1H), 3.40 (s, 3H), 2.60 (m, 2H), 1.00–2.20 (m, 19H); MS [M+H]$^+$476.

Example 25

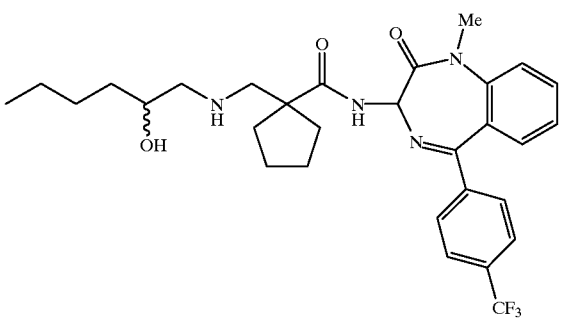

The title compound was prepared using the method as described below.

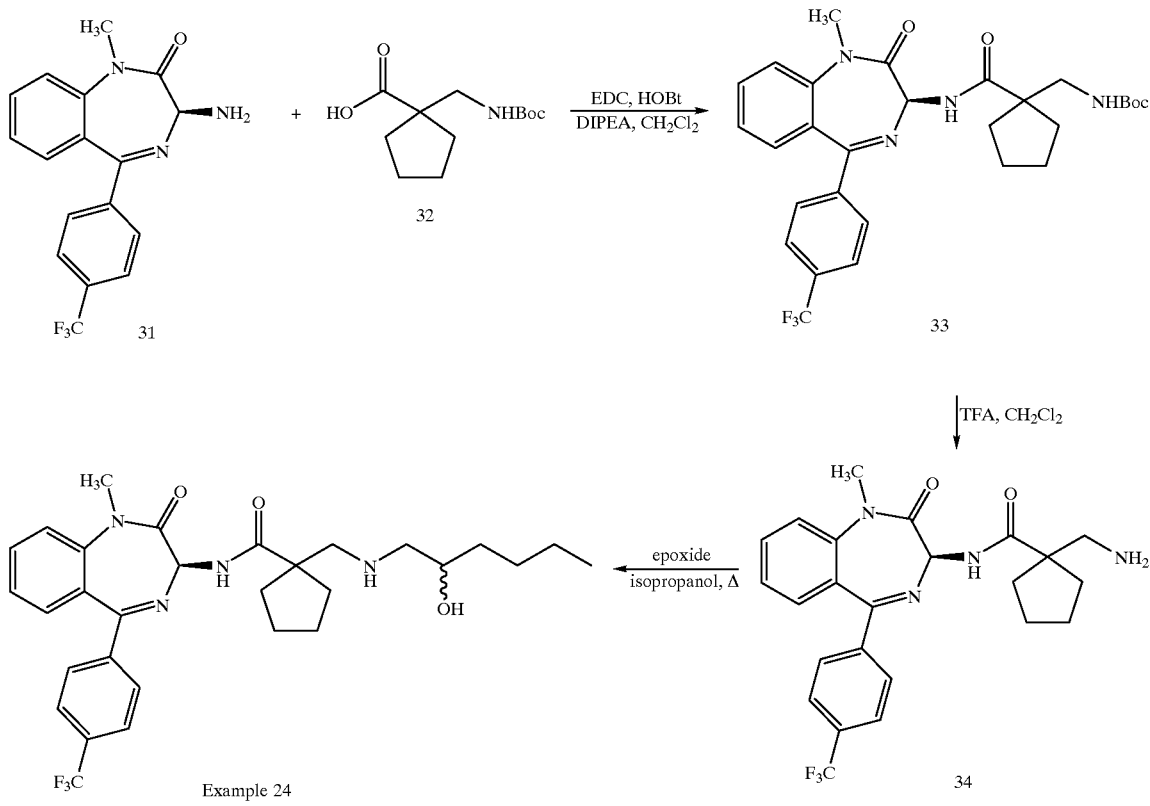

Preparation of Intermediate 33

To a stirred solution of acid 32 (397 mg, 1.6 mmol) was added HOBt (226 mg, 1.7 mmol), EDC (312 mg, 1.6 mmol) and DIPEA (1.0 mL, 5.9 mmol). The reaction was stirred 15 min and benzodiazepine 31, (see Example 3), was added in one portion and the reaction stirred overnight. Water was added and the layers separated. The organic layer was washed with 5% sodium bicarbonate and brine. The organic solution was dried over magnesium sulfate, filtered and concentrated. The residue was chromatographed in 50% ethyl acetate in hexanes to provide 33 as an oil. The oil was dissolved in ether. Hexanes were added and the mixture evaporated to provide 33 (736 mg, 88%) as a white solid: $^1$H NMR (300 MHz, CDCl$_3$) δ6 7.71 (d, 2H), 7.67 (d, 2H), 7.61 (m, 1H), 7.41 (d, 1H), 7.3–7.2 (m, 3H) 5.53 (m, 1H), 5.51 (d, 1H), 3.48 (s, 3H), 3.31 (t, 2H), 2.11–1.99 (m, 2H), 1.78 (m, 6H), 1.45 (s, 9H).

Preparation of Intermediate 34

To a stirred solution of 33 (730 mg, 1.3 mmol) in methylene chloride (10 mL) was added trifluoroacetic acid (10 mL) and the reaction stirred 4 h. The reaction was evaporated and chromatographed over silica gel with a 1:1 mixture of ethyl acetate and 6:3:1 chloroform, methanol, and ammonium hydroxide. The eluent was concentrated and methanol added. The solution was evaporated and chromatographed in a 1:1 mixture of ethyl acetate and 6:3:1 chloroform, methanol, and ammonium hydroxide to provide 34 (550 mg, 91%) as a white solid: $^1$H NMR (CDCl$_3$) δ9.17 (d, 1H), 7.73 (d, 2H), 7.62 (d, 2H), 7.62–7.52 (m, 1H), 7.36 (d, 1H), 7.33–7.17 (m, 2H), 5.58 (d, 1H), 3.50 (s, 3H), 2.98 (s, 2H), 2.26–2.10 (m, 2H), 1.88–1.48 (m, 8H).

Preparation of Example 25

To a stirred solution of 34 (70 mg, 0.15 mmol) in isopropanol (0.5 mL) was added 1,2 epoxyhexane (18 μL, 0.15 mmol) and the reaction vial capped and heated at 80° C. for 12 h. Additional 1,2 epoxyhexane (~40 μL) was added and the reaction heated an additional 18 h. The reaction was concentrated and chromatographed over silica gel in ethyl acetate to provide the title compound Example 25 (54 mg, 63%) as a white solid: mp 61–70° C.; $^1$H NMR (300 MHz, CDCl$_3$) δ10.38 (dd, 1H), 7.75 (d, 2H), 7.65 (d, 2H), 7.65–7.55 (m, 1H), 7.39 (d, 1H), 7.30–7.20 (m, 2H), 5.55 (d, 1H), 3.92 (m, 1H), 3.70 (m, 1H), 3.48 (s, 3H), 2.93–2.73 (m, 3H), 2.60 (t, 1H), 2.30–2.03 (m, 2H), 1.83–1.20 (m, 12H), 0.88 (m, 4H); IR (KBr) 3432, 2955, 1662, 1522, 1324, 1129, 1067 cm$^{-1}$; ESI MS m/z=559 [C$_{30}$H$_{37}$F$_3$N$_4$O$_3$+H]$^+$; HPLC>95%, t$_r$=18.81 min. using HPLC condition A.

Example 26

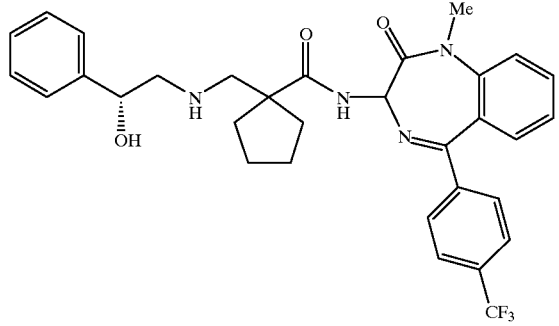

The title compound was prepared using the method similar to that described for Example 25. The product was obtained as a white solid (20 mg, 23%): mp 82–86° C.; $^1$H NMR (300 MHz, CDCl$_3$) δ10.30 (d, 1H), 7.73 (d, 2H), 7.63 (d, 2H), 7.63–7.53 (m, 1H), 7.36 (d, 2H), 7.35–7.20 (m, 8H), 5.60 (d, 1H), 4.90 (d, 1H), 4.45 (broad s, 1H), 3.50 (s, 3H), 3.0–2.8 (m, 4H), 2.3–2.1 (m, 2H), 1.84–1.45 (m, 5H); IR (neat) 3424, 2951, 1658, 1518, 1323, 1127 cm$^{-1}$; ESI MS m/z=579 [C$_{32}$H$_{33}$F$_3$N$_4$O$_3$+H]$^+$; HPLC>95%, t$_r$=20.11 min. using HPLC condition A.

Example 27

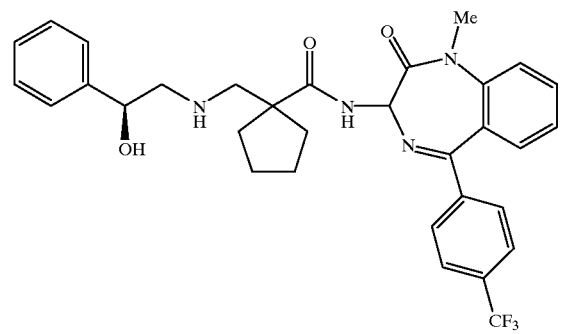

The title compound was prepared using the method similar to that described for Example 25. The product was obtained as a white solid (35 mg, 40%): mp 86–90° C., $^1$H NMR (300 MHz, CDCl$_3$) δ10.2 (s, 1H), 7.73 (d, 2H), 7.60 (d, 2H), 7.65–7.59 (m, 1H), 7.40 (d, 1H), 7.35 (t, 1H), 7.25–7.18 (6H), 5.58 (d, 1H), 4.92 (d, 1H), 4.5 (broad s, 1H), 3.5 (s, 3H), 3.0–2.8 (m, 4H), 2.3–2.1 (m, 2H), 1.9–1.4 (m, 9H); IR (KBr) 3424, 2952, 1663, 1324, 1127 cm$^{-1}$; ESI MS m/z=579 [C$_{32}$H$_{33}$F$_3$N$_4$O$_3$+H]$^+$; HPLC>95%, t$_r$=18.73 min. using HPLC condition A.

Example 28

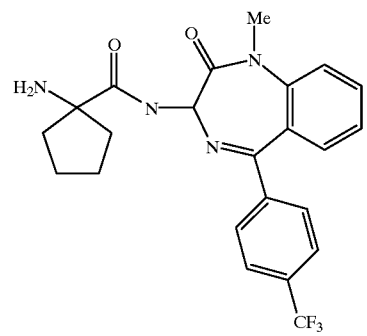

The title compound was prepared in a manner similar to that described for Example 22 using the amino benzodiazepine employed in Example 3. The product was obtained as oil. $^1$H NMR (300 MHz, CD$_3$OD) δ7.20–7.80 (m, 8H), 5.45 (m, 1H), 3.45 (s, 3H), 2.20 (m, 3H), 2.00–1.60 (m, 5H). MS [M+H]$^+$445.

Tables 1–4 below provide representative Examples of the compounds of Formula (I) of the present invention.

TABLE 1

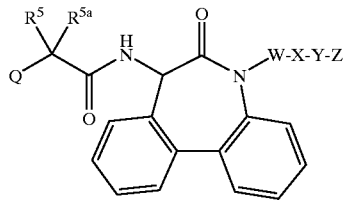

| Ex. # | Q | CR⁵R⁵ᵃ | -WXYZ |
|---|---|---|---|
| 1 | [(3-Me-butyl)amino]-methyl | cyclopentyl | Me |
| 2 | [N'-(ethoxycarbonyl)-N'-(3-Me-butyl)amino]-methyl | cyclopentyl | Me |
| 4 | [(3-Me-butyl)amino]-methyl | perhydro-2H-pyran | Me |
| 8 | 2-hydroxy-pentyl | cyclopentyl | Me |
| 9 | [(3,5-diF-benzyl)C(=O)NH]-methyl | perhydro-2H-pyran | Me |
| 11 | [(1-hydroxy-2-Me-propyl)C(=O)NH]-methyl | cyclopentyl | Me |
| 12 | [(1-hydroxy-3-Me-butyl)C(=O)NH]-methyl | cyclopentyl | Me |
| 13 | [(3,5-diF-benzyl)C(=O)NH]-methyl | cyclopentyl | Me |
| 16 | 2-[(2-Me-propyl)amino]-ethyl | cyclopentyl | Me |
| 17 | 2-[(cyclopropylmethyl)amino]-ethyl | cyclopentyl | Me |
| 18 | [(3,5-diF-phenethyl)amino]-methyl | cyclopentyl | Me |
| 19 | [(1,4-diF-benzyl)amino]-methyl | cyclopentyl | Me |
| 20 | [(2-cyclopentylethyl)amino]-methyl | cyclopentyl | Me |
| 22 | (2-hydroxy-4-Me-pentyl)amino | cyclopentyl | Me |
| 23 | (2-hydroxy-3-Me-butyl)amino | cyclopentyl | Me |
| 24 | (2-cyclohexyl-2-hydroxy-ethyl)amino | cyclopentyl | Me |

TABLE 2

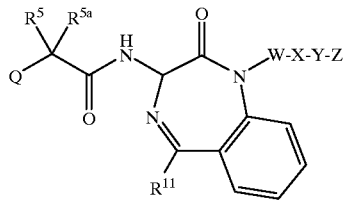

| Ex. # | Q | CR⁵R⁵ᵃ | -WXYZ | R¹¹ |
|---|---|---|---|---|
| 3 | [(3-Me-butyl)amino]-methyl | cyclopentyl | Me | 4-CF₃-phenyl |
| 5 | 5-Me-hexyl | cyclopentyl | Me | phenyl |
| 6 | n-pentyl | cyclopentyl | Me | phenyl |
| 7 | 2-hydroxy-pentyl | cyclohexyl | Me | phenyl |
| 10 | [(1-hydroxy-2-Me-propyl)-C(=O)NH]-methyl | cyclopentyl | Me | 4-CF₃-phenyl |
| 15 | [(1-hydroxy-2-Me-propyl)-C(=O)NH]-methyl | cyclopentyl | Me | cyclopentyl |
| 21 | (cyclohexylamino)-methyl | cyclopentyl | Me | phenyl |
| 25 | [(2-hydroxy-hexyl)amino]-methyl | cyclohexyl | Me | 4-CF₃-phenyl |
| 26* | [(2-hydroxy-2-phenyl)-ethylamino]-methyl | cyclohexyl | Me | 4-CF₃-phenyl |
| 27* | [(2-hydroxy-2-phenyl)-ethylamino]-methyl | cyclohexyl | Me | 4-CF₃-phenyl |

*stereoisomer

TABLE 3

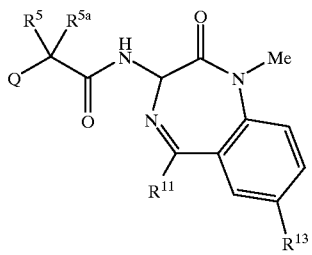

| Ex. # | Q | CR⁵R⁵ᵃ | R¹¹ | R¹³ |
|---|---|---|---|---|
| 14 | [(1-hy-droxy-2-Me-propyl)-C(=O)NH]-methyl | cyclo-pentyl | phen-yl | F |

UTILITY

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γsecretase activity, either directly or indirectly, control the production of Aβ. Such inhibition of β or γsecretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including J.Med.Chem. 1999, 42, 3889–3898; PCT publication number WO 98/22493, EPO publication number 0652009; U.S. Pat. No. 5,703,129; and U.S. Pat. No. 5,593,846; all hereby incorporated by reference.

The compounds of the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an $IC_{50}$ or $K_i$ value of less than about 100 μM for the inhibition of Aβ production. Preferably the $IC_{50}$ or $K_i$ value is less than about 10 μM; more preferably the $IC_{50}$ or $K_i$ value is less than about 0.1 μM. The present invention has been shown to inhibit Aβ protein production with an $IC_{50}$ or $K_i$ value of less than 100 μM.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 μl normal mouse serum and 50 μl of protein A Sepharose (Pharmacia), mixed by end-over-end rotation for 30 minutes at 4° C., followed by a brief centrifugation in a microfuge. The supernatant is then harvested and transferred to fresh tubes containing 5 μg of a monoclonal antibody (clone 1101.1; directed against an internal peptide sequence in Aβ) and 50 μl protein A Sepharose. After incubation overnight at 4° C., the samples are washed three times with high salt washing buffer (50 mM Tris, pH 7.5, 5 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an $IC_{50}$ less than 100 μM.

C-Terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150mM NaCl, 0.125% NaN₃). Again, lysates are precleared with 5 μl normal rabbit serum/50 μl protein A Sepharose, followed by the addition of BC-1 antiserum (15 μl;) and 50 μl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 μM.

Aβ Immunoprecipitation Assay

This immunoprecipitation assay is specific for γ secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and Aβ is isolated from the conditioned medium and C-terminal fragments from cell lysates (see above). The test compounds are characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 μM.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I):

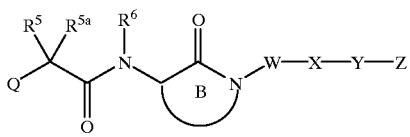

(I)

or a stereoisomer or a pharmaceutically acceptable salt thereof, wherein:

Q is
—$(CR^7R^{7a})_m$—$R^4$,
—$(CR^7R^{7a})_m$—CH(OH)—$R^4$,
—$(CR^7R^{7a})_m$—NHC(O)—$R^4$,
—$(CR^7R^{7a})_n$—S—$R^4$,
—$(CR^7R^{7a})_n$—O—$R^4$,
—$(CR^7R^{7a})_n$—N($R^{7b}$)—$R^4$,
—$(CR^7R^{7a})_n$—S(=O)—$R^4$, or
—$(CR^7R^{7a})_n$—C(=O)—$R^4$;

m is 1, 2, or 3;
n is 0, 1, or 2;
$R^4$ is H,
$C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$, aryl substituted with 0-3 $R^{4b}$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $CF_3$, $C_1$-$C_3$ alkyl,
$C_3$-$C_{10}$ carbocycle substituted with 0-3 $R^{4b}$, aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^5$ and $R^{5a}$ are combined to form a 3-8 membered carbocyclic moiety;
wherein said 3-8 membered carbocyclic moiety is saturated or partially unsaturated;
wherein said 3-8 membered carbocyclic moiety may optionally contain the heteroatom —O—; and
wherein said 3-8 membered carbocyclic moiety is substituted with 0-2 $R^{5b}$;

$R^{5b}$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$; $R^6$ is H;
$C_1$-$C_6$ alkyl substituted with 0-3 $R^{6a}$;
$C_3$-$C_{10}$ carbocycle substituted with 0-3 $R^{6b}$; or
aryl substituted with 0-3 $R^{6b}$;

$R^{6a}$, at each occurrence, is independently selected from H, $C_1$-$C_6$ alkyl, $OR^{14}$, Cl, F, Br, I, (=O), CN, $NO_2$, $NR^{15}R^{16}$, aryl and $CF_3$;

$R^{6b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;

$R^7$, at each occurrence, is independently H or $C_1$-$C_4$ alkyl;

$R^{7a}$, at each occurrence, is independently H or $C_1$-$C_4$ alkyl;

$R^{7b}$ is H, $C_1$-$C_4$ alkyl, or ($C_1$-$C_4$ alkyl)OC(=O)—;

Ring B is

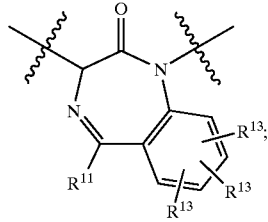

$R^{11}$, at each occurrence, is independently selected from H, $C_1$-$C_4$ alkoxy, Cl, F, Br, I, CN, $NO_2$, $NR^{18}R^{19}$, C(=O)$R^{17}$, C(=O)O$R^{17}$, C(=O)$NR^{18}R^{19}$, S(=O)$_2NR^{18}R^{19}$, $CF_3$;
$C_1$-$C_6$ alkyl optionally substituted with 0-3 $R^{11a}$;
aryl substituted with 0-3 $R^{11b}$;
$C_3$-$C_{10}$ carbocycle substituted with 0-3 $R^{11b}$; and
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, (=O)$_0$, CN, $NO_2$, $NR^{15}R^{16}$, $CF_3$;
phenyl substituted with 0-3 $R^{11b}$; $C_3$-$C_6$ cycloalkyl substituted with 0-3 $R^{11b}$; and
5 to 6 membered heterocycle containing 1 to 4 heteroatoms selected from nitrogen, oxygen, and sulphur, wherein said 5 to 6 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(—O)$_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

W is a bond or —$(CR^8R^{8a})_p$—;

p is 0, 1, 2, 3, or 4;

$R^8$ and $R^{8a}$, at each occurrence, are independently selected from H, F, $C_1-C_4$ alkyl, $C_2-C_4$ alkenyl, $C_2-C_4$ alkynyl and $C_3-C_8$ cycloalkyl;

X is a bond;
 aryl substituted with 0–3 $R^{Xb}$;
 $C_3-C_{10}$ carbocycle substituted with 0–3 $R^{Xb}$; or
 5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ halothioalkoxy;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, $C_1-C_6$ alkyl or $C_3-C_8$ cycloalkyl;

V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(O)$_2$$NR^{19b}$—, —$NR^{19b}$S(=O)—, —S(=O)$NR^{19b}$—, —C(=O)O—, or —OC(=O)—;

Z is H;
 $C_1-C_8$ alkyl substituted with 0–3 $R^{12a}$;
 $C_2-C_6$ alkenyl substituted with 0–3 $R^{12a}$;
 $C_2-C_6$ alkynyl substituted with 0–3 $R^{12a}$;
 aryl substituted with 0–4 $R^{12b}$;
 $C_3-C_{10}$ carbocycle substituted with 0–4 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—,
 aryl substituted with 0–4 $R^{12b}$;
 $C_3-C_{10}$ carbocycle substituted with 0–4 $R^{12b}$; and
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, aryl, $C_3-C_6$ cycloalkyl, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^{13}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

$R^{14}$ is H, phenyl, benzyl, $C_1-C_6$ alkyl, $C_2-C_6$ alkoxyalkyl, or $C_3-C_6$ cycloalkyl;

$R^{14a}$ is H, phenyl, benzyl, or $C_1-C_4$ alkyl;

$R^{15}$, at each occurrence, is independently selected from H, $C_1-C_6$ alkyl, benzyl, phenethyl, $(C_1-C_6$ alkyl)-C(=O)—, and $(C_1-C_6$ alkyl)-S(=O)$_2$—;

$R^{16}$, at each occurrence, is independently selected from H, OH, $C_1-C_6$ alkyl, benzyl, phenethyl, $(C_1-C_6$ alkyl)-C(=O)—, and $(C_1-C_6$ alkyl)-S(=O)$_2$—;

$R^{17}$ is H, $C_1-C_6$ alkyl, $C_2-C_6$ alkoxyalkyl,
 aryl substituted by 0–4 $R^{17a}$, or
 —$CH_2$-aryl substituted by 0–4 $R^{17a}$;

$R^{17a}$ is H, methyl, ethyl, propyl, butyl, methoxy, ethoxy, propoxy, butoxy, -OH, F, Cl, Br, I, $CF_3$, $OCF_3$, $SCH_3$, $S(O)CH_3$, $SO_2CH_3$, —$NH_2$, —$N(CH_3)_2$, or $C_1-C_4$ haloalkyl;

$R^{18}$, at each occurrence, is independently selected from H, $C_1-C_6$ alkyl, aryl, aryl-$CH_2$—, aryl-$CH_2CH_2$—, $(C_1-C_6$ alkyl)-C(=O)—, and $(C_1-C_6$ alkyl)-S(=O)$_2$—;

$R^{19}$, at each occurrence, is independently selected from Ii, OH, $C_1-C_6$ alkyl, aryl, aryl-$CH_2$—, aryl-$CH_2CH_2$—, $(C_1-C_6$ alkyl)-C(=O)—, and $(C_1-C_6$ alkyl)-S(=O)$_2$—; and $R^{19b}$, at each occurrence, is independently is H or $C_1-C_4$ alkyl;

provided when Q is —$(CR^7R^{7a})_n$—N($R^{7b}$)—$R^4$ and $R^{7b}$ is $(C_1-C_4$ alkyl)OC(=O)—, then n is 1 or 2; and provided when Q is —$(CR^7R^{7a})_n$—N($R^{7b}$)—$R^4$ and n is 0, then $R^4$ does not contain a —C(=O)— adjacent to —N($R^{7b}$)—.

2. A compound, according to claim 1, of Formula (I) or a stereoisomer or a pharmaceutically acceptable salt thereof, wherein:

Q is
 —$(CR^7R^{7a})_m$—$R^4$,
 —$(CR^7R^{7a})_n$—CH(OH)—$R^4$,
 —$(CR^7R^{7a})_m$—NHC(=O)—$R^4$,
 —$(CR^7R^{7a})_n$—S—$R^4$,
 —$(CR^7R^{7a})_n$—O—$R^4$, or
 —$(CR^7R^{7a})_n$—N($R^{7b}$)—$R^4$;

m is 0 or 2;

n is 0 or 1;

$R^4$ is H,
 $C_1-C_8$ alkyl substituted with 0–3 $R^{4a}$,
 $C_2-C_8$ alkenyl substituted with 0–3 $R^{4a}$,
 $C_2-C_8$ alkynyl substituted with 0–3 $R^{4a}$,
 $C_3-C_{10}$ carbocycle substituted with 0–3 $R^{4b}$, aryl substituted with 0–3 $R^{4b}$, or
 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, OH, F, Cl, Br, I, $CF_3$. $C_1-C_3$ alkyl,
 $C_3-C_{10}$ carbocycle substituted with 0–3 $R^{4b}$, aryl substituted with 0–3 $R^{4b}$, and
 5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
 $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^5$ and $R^{5a}$ are combined to form a 3–8 membered carbocyclic moiety;
 wherein said 3–8 membered carbocyclic moiety is saturated or partially unsaturated;
 wherein said 3–8 membered carbocyclic moiety may optionally contain the heteroatom —O—; and wherein said 3–8 membered carbocyclic moiety is substituted with 0–2 $R^{5b}$;

$R^{5b}$, at each occurrence, is independently selected from H, OH, Cl, F, Br, I, CN, $NO_2$, $CF_3$, acetyl, $SCH_3$, methyl, ethyl, methoxy, ethoxy, allyl, $-OCF_3$, and $-SCF_3$;

$R^6$ is H, methyl, or ethyl;

$R^7$, at each occurrence, is independently H or $C_1-C_4$ alkyl;

$R^{7a}$, at each occurrence, is independently H or $C_1-C_4$ alkyl;

$R^{7b}$ is H, $C_1-C_4$ alkyl, or ($C_1-C_4$ alkyl)OC(=O)—;

Ring B is

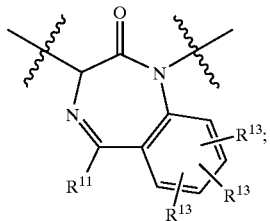

$R^{11}$, at each occurrence, is independently selected from H, $C_1-C_4$ alkoxy, Cl, F, Br, I, CN, $NO_2$, $NR^{18}R^{19}$, C(=O)$R^{17}$, C(=O)$OR^{17}$, C(=O)$NR^{18}R^{19}$, S(=O)$_2NR^{18}R^{19}$, $CF_3$;

$C_1-C_6$ alkyl optionally substituted with 0–3 $R^{11a}$; aryl substituted with 0–3 $R^{11b}$;

$C_3-C_{10}$ carbocycle substituted with 0–3 $R^{11b}$; and 5 to 10 membered heterocycle containing 1 to 4 heteroatoms selected from nitrogen, oxygen, and sulphur, wherein said 5 to 10 membered heterocycle 0 is substituted with 0–3 $R^{11b}$;

$R^{11a}$, at each occurrence, is independently selected from H, $C_1-C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3-C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle D is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl-, $SCH_3$, S(=O)$CH_3$, S(=O)$_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

W is a bond or —(CH$_2$)$_p$—;

p is 1 or 2;

X is a bond;

phenyl substituted with 0–2 $R^{Xb}$;

$C_3-C_6$ carbocycle substituted with 0–2 $R^{Xb}$; or 5 to 6 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1-C_4$ alkyl, $C_1-C_3$ alkoxy, $C_1-C_3$ haloalkyl, $C_1-C_3$ haloalkoxy, and $C_1-C_3$ halothioalkoxy;

Y is a bond, —C(=O)—, —O—, —S—, —S(=O)—, —S(=O)$_2$—, —N($R^{19}$)—, —C(=O)N$R^{19b}$, —N$R^{19b}$C(=O)—, —N$R^{19b}$S(=O)$_2$—, —S(=O)$_2$N$R^{19b}$—, —N$R^{19b}$S(=O), —S(=O)N$R^{19b}$, —C(=O)O—, or —OC(=O)—;

Z is H;

$C_1-C_8$ alkyl substituted with 0–3 $R^{12a}$;

$C_2-C_6$ alkenyl substituted with 0–3 $R^{12a}$;

$C_2-C_6$ alkynyl substituted with 0–3 $R^{12a}$;

aryl substituted with 0–4 $R^{12b}$;

$C_3-C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, -C(=O)$NR^{15}R^{16}$, $CF_3$, acetyl, $SCH_3$, S(=O)$CH_3$, S(=O)$_2$$CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—, aryl substituted with 0–4 $R^{12b}$;

$C_3-C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^{13}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

$R^{14}$ is H, phenyl, benzyl, $C_1-C_6$ alkyl, $C_2-C_6$ alkoxyalkyl, or $C_3-C_6$ cycloalkyl;

$R^{14a}$ is H, phenyl, benzyl, or $C_1-C_4$ alkyl;

$R^{15}$, at each occurrence, is independently selected from H, $C_1-C_6$ alkyl, benzyl, phenethyl, ($C_1-C_6$ alkyl)-C(=O)—, and ($C_1-C_6$ alkyl)-S(=O)$_2$—;

$R^{16}$, at each occurrence, is independently selected from H, OH, $C_1-C_6$ alkyl, benzyl, phenethyl, ($C_1-C_6$ alkyl)-C(=O)—, and ($C_1-C_6$ alkyl)-S(=O)$_2$—;

$R^{17}$ is H, $C_1-C_6$ alkyl, $C_2-C_6$ alkoxyalkyl, aryl substituted by 0–4 $R^{17a}$, or —CH$_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1-C_4$ haloalkyl;

$R^{18}$, at each occurrence, is independently selected from H, $C_1-C_6$ alkyl, phenyl, benzyl, phenethyl, ($C_1-C_6$ alkyl)-C(=O)—, and ($C_1-C_6$ alkyl)-S(=O)$_2$—;

$R^{19}$, at each occurrence, is independently selected from H, OH, methyl, ethyl, propyl, butyl, phenyl, benzyl, and phenethyl; and $R^{19b}$, at each occurrence, is independently is H or $C_1-C_4$ alkyl;

provided when Q is —(CR$^7$R$^{7a}$)$_n$—N(R$^{7b}$)—R$^4$ and R$^{7b}$ is ($C_1-C_4$ alkyl)OC(=O)—, then n is 1 or 2; and provided when Q is —(CR$^7$R$^{7a}$)$_n$—N(R$^{7b}$)—R$^4$ and n is 0, then R$^4$ does not contain a —C(=O)— adjacent to —N(R$^{7b}$)—.

3. A compound, according to claim 2, of Formula (Ia)

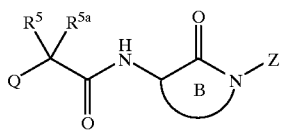

(Ia)

or a stereoisomer or a pharmaceutically acceptable salt thereof, wherein:

Q is
—(CHR$^{7a}$)$_m$—R$^4$,
—(CHR$^{7a}$)$_m$—CH(OH)—R$^4$,
—(CHR$^{7a}$)$_m$—NHC(=O)—R$^4$,
—(CHR$^{7a}$)$_n$—S—R$^4$,
—(CHR$^{7a}$)$_n$—O—R$^4$, or
—(CHR$^{7a}$)$_n$—N(R$^{7b}$)—R$^4$;

m is 1 or 2;

n is 0 or 1;

R$^4$ is H,
$C_1$-$C_8$ alkyl substituted with 0–3 R$^{4a}$,
$C_2$-$C_8$ alkenyl substituted with 0–3 R$^{4a}$,
$C_2$-$C_8$ alkynyl substituted with 0–3 R$^{4a}$,
$C_3$-$C_{10}$ carbocycle substituted with 0–3 R$^{4b}$, aryl substituted with 0–3 R$^{4b}$, or
5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4a}$, at each occurrence, is independently selected from H, OH, F, Cl, Br, I, CF$_3$, methyl, ethyl,
$C_3$-$C_{10}$ carbocycle substituted with 0–3 R$^{4b}$, aryl substituted with 0–3 R$^{4b}$, and
5 to 10 membered heterocycle containing 1 to 4 heteroatoms selected from nitrogen, oxygen, and sulphur, wherein said 5 to 10 membered heterocycle is substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

R$^5$ and R$^{5a}$ are combined to form a 3–8 membered carbocyclic moiety;
wherein said 3–8 membered carbocyclic moiety is saturated or partially unsaturated;
wherein said 3–8 membered carbocyclic moiety may optionally contain the heteroatom —O—; and
wherein said 3–8 membered carbocyclic moiety is substituted with 0–2 R$^{5b}$;

R$^{5b}$, at each occurrence, is independently selected from H, OH, Cl, F, CN, CF$_3$, methyl, ethyl, methoxy, ethoxy, allyl, and —OCF$_3$;

R$^{7a}$, at each occurrence, is independently H, methyl, or ethyl;

R$^{7b}$ is H, methyl, ethyl, CH$_3$OC(=O)—, or CH$_3$CH$_2$OC(=O)—;

Ring B is

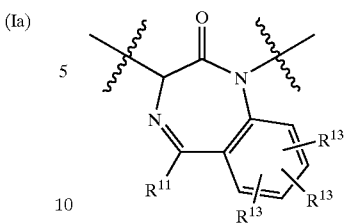

R$^{11}$, at each occurrence, is independently selected from H, $C_1$-$C_4$ alkoxy, Cl, F, Br, I, CN, NO$_2$, NR$^{18}$R$^{19}$, C(=O)R$^{17}$, C(=O)OR$^{17}$, C(=O)NR$^{18}$R$^{19}$, S(O)$_2$NR$^{18}$R$^{19}$, CF$_3$;
$C_1$-$C_6$ alkyl optionally substituted with 0–3 R$^{11a}$; aryl substituted with 0–3 R$^{11b}$;
$C_3$-$C_{10}$ carbocycle substituted with 0–3 R$^{11b}$; and
5 to 10 membered heterocycle containing 1 to 4 heteroatoms selected from nitrogen, oxygen, and sulphur, wherein said 5 to 10 membered heterocycle is substituted with 0–3 R$^{11b}$;

R$^{11a}$, at each occurrence, is independently selected from H, $C_1$-$C_6$ alkyl, OR$^{14}$, Cl, F, Br, I, =O, CN, NO$_2$, NR$^{15}$R$^{16}$, CF$_3$;
phenyl substituted with 0–3 R$^{11b}$;
$C_3$-$C_6$ cycloalkyl substituted with 0–3 R$^{11b}$; and
5 to 6 membered heterocycle containing 1 to 4 heteroatoms selected from nitrogen, oxygen, and sulphur, wherein said 5 to 6 membered heterocycle is substituted with 0–3 R$^{11b}$;

R$^{11b}$, at each occurrence, is independently selected from H, OH, Cl, F, Br, I, CN, NO$_2$, NR$^{15}$R$^{16}$, CH$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

W is a bond;

X is a bond;

Y is a bond;

Z is H;
$C_1$-$C_8$ alkyl substituted with 0–3 R$^{12a}$;
$C_2$-$C_6$ alkenyl substituted with 0–3 R$^{12a}$;
$C_2$-$C_6$ alkynyl substituted with 0–3 R$^{12a}$; aryl substituted with 0–4 R$^{12b}$;
$C_3$-$C_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$RI-6, -C(=O)NR$^{15}$R$^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, aryl substituted with 0–4 R$^{12b}$;
$C_3$-$C_{10}$ carbocycle substituted with 0–4 R$^{12b}$; and
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{2-6}$, CF$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{16}$, at each occurrence, is independently selected from H, OH, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{17}$ is H, $C_1$-$C_6$ alkyl, $C_2$-$C_6$ alkoxyalkyl,
aryl substituted by 0-4 $R^{17a}$, or
—$CH_2$—aryl substituted by 0-4 $R^{17a}$;

$R^{17a}$ is H, methyl, ethyl, propyl, butyl, methoxy, ethoxy, propoxy, butoxy, —OH, F, Cl, Br, I, $OF_3$, $OCF_3$, $SCH_3$, $S(O)CH_3$, $SO_2CH_3$, —$NH_2$, —$N(CH_3)_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;

$R^{19}$, at each occurrence, is independently selected from H, OH, methyl, ethyl, propyl, butyl, phenyl, benzyl, and phenethyl;

provided when Q is —$(CHR^{7a})_n$—$N(R^{7b})$—$R^4$ and $R^{7b}$ is ($C_1$-$C_4$ alkyl)OC(=O)—, then n is 1 or 2; and provided when Q is —$(CHR^{7a})_n$—$N(R^{7b})$—$R^4$ and n is 0, then $R^4$ does not contain a —C(=O)— adjacent to —$N(R^{7b})$—.

4. A compound according to claim 3 of Formula (Ia) or a stereoisomer or a pharmaceutically acceptable salt thereof, wherein:

Q is
—$(CH_2)_n$—$R^4$,
—$(CH_2)_m$—CH(OH)$R^4$,
—$(CH_2)_m$—NHC(O)$R^4$,
—$(CH_2)_n$—S—$R^4$, or
—$(CH_2)_n$—$N(R^{7b})$—$R^4$;

m is 1 or 2;
n is 0 or 1;
$R^4$ is
$C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$, aryl substituted with 0-3 $R^{4b}$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $CF_3$, methyl,
$C_3$-$C_{10}$ carbocycle substituted with 0-3 $R^{4b}$, aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^5$ and $R^{5a}$ are combined to form a 3-8 membered carbocyclic moiety;
wherein said 3-8 membered carbocyclic moiety is saturated or partially unsaturated; and
wherein said 3-8 membered carbocyclic moiety may optionally contain the heteroatom —O—;

$R^{7b}$ is H, methyl, ethyl, $CH_3OC(=O)$—, or $CH_3CH_2OC(=O)$—;

Ring B is

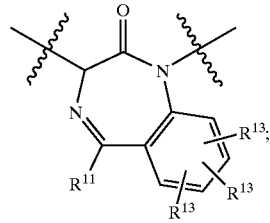

$R^1$, at each occurrence, is independently selected from H, $NR^{18}R^{19}$, $CR^3$;
$C_1$-$C_4$ alkyl optionally substituted with 0-1 $R^{11a}$; phenyl substituted with 0-3 $R^{11b}$;
$C_3$-$C_6$ carbocycle substituted with 0-3 $R^{11b}$; and
5 to 6 membered heterocycle containing 1 to 4 heteroatoms selected from nitrogen, oxygen, and sulphur, wherein said 5 to 6 membered heterocycle is substituted with 0-3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$-$C_4$ alkyl, $OR^{14}$, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond;
X is a bond;
Y is a bond;
Z is H;
$C_1$-$C_8$ alkyl substituted with 0-3 $R^{12a}$;
$C_2$-$C_6$ alkenyl substituted with 0-3 $R^{12a}$; or
$C_2$-$C_6$ alkynyl substituted with 0-3 $R^{12a}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl,
$C_1$-$C_4$ haloalkoxy, $C_1$-$C_4$ haloalkyl-S—, aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, and phenethyl;

provided when Q is —$(CH_2)_n$—$N(R^{7a})$—$R^4$ and $R^{7b}$ is —($C_1$–$C_4$ alkyl)OC(=O)—, then n is 1 or 2; and provided when Q is —$(CH_2)_n$—$N(R^{7b})$—$R^4$ and n is 0, then $R^4$ does not contain a —C(=O)— adjacent to —$N(R^{7b})$—.

5. A compound according to claim 4 wherein:

Q is
—$CH_2R^4$, —$CH_2CH_2R^4$, —$CH_2CH(OH)$—$R^4$, —$CH_2NH$—$R^4$, —$CH_2CH_2NHR^4$, —$CH_2N(R^{7b})$—$R^4$, —$CH_2NHC(=O)$—$R^4$, or —NH—$R^4$;

$R^4$ is
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_6$ carbocycle substituted with 0–3 $R^{4b}$, phenyl substituted with 0–3 $R^{4b}$, or
5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4a}$, at each occurrence, is independently selected from H, OH, F, Cl, Br, I, $CF_3$, methyl,
$C_3$–$C_6$ carbocycle substituted with 0–3 $R^{4b}$,
phenyl substituted with 0–3 $R^{4b}$, and
5 to 6 membered heterocycle containing 1 to 3 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ and $R^{5a}$ are combined to form a 3–6 membered carbocyclic moiety;
wherein said 3–6 membered carbocyclic moiety is saturated or partially unsaturated; and
wherein said 3–6 membered carbocyclic moiety may optionally contain the heteroatom —O—;

$R^{7b}$ is I—I, methyl, ethyl, $CH_3OC(=O)$—, or $CH_3CH_2OC(O)$—;

Ring B is

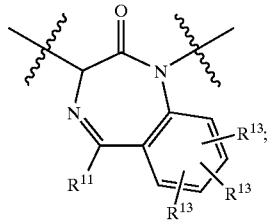

$R^{11}$, at each occurrence, is independently selected from H, $NR^{18}R^{19}$, $CF_3$;
$C_1$–$C_4$ alkyl optionally substituted with 0–1 $R^{11a}$; phenyl substituted with 0–3 $R^{11b}$;
$C_3$–$C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$. or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_4$ alkyl substituted with 0–3 $R^{12a}$,
$C_2$–$C_4$ alkenyl substituted with 0–3 $R^{12a}$, or
$C_2$–$C_4$ alkynyl substituted with 0–3 $R^{12a}$, $R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and provided when Q is —NH—$R^4$, then $R^4$ does not contain a —C(=O)— adjacent to —$N(R^{7b})$—.

6. A compound according to claim 5 or a stereoisomer or a pharmaceutically acceptable salt thereof wherein:

Q is —$CH_2R^4$, —$CH_2CH_2R^4$, —$CH_2CH(OH)$—$R^4$, —$CH_2NH$—$R^4$, —$CH_2CH_2NHR^4$, —$CH_2N(R^{7b})$—$R^4$, —$CH_2NHC(=O)$—$R^4$, or —NH—$R^4$;

83

R⁴ is
  C₁–C₆ alkyl substituted with 0–3 $R^{4a}$,
  C₂–C₆ alkenyl substituted with 0–3 $R^{4a}$,
  C₂–C₆ alkynyl substituted with 0–3 $R^{4a}$,
  C₃–C₆ carbocycle substituted with 0–3 $R^{4b}$, or
  phenyl substituted with 0–3 $R^{4b}$;

$R^{4a}$, at each occurrence, is independently selected from H, OH, F, Cl, Br, I, CF₃, methyl,
  C₃–C₆ carbocycle substituted with 0–3 $R^{4b}$,
  phenyl substituted with 0–3 $R^{4b}$, and
  5 to 6 membered heterocycle containing 1 to 3 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, NO₂, $NR^{15}R^{16}$, CF₃, acetyl, SCH₃, S(=O)CH₃, S(=O)₂CH₃,
  C₁–C₆ alkyl, C₁–C₄ alkoxy, C₁–C₄ haloalkyl,
  C₁–C₄ haloalkoxy, and C₁–C₄ haloalkyl-S—;

R⁵ and $R^{5a}$ are combined to form a 3–6 membered carbocyclic moiety selected from cyclopropyl, cyclobutyl, cyclopentyl, cyclohexyl, and perhydro-2H-pyran;

$R^{7b}$ is H, methyl, ethyl, CH₃OC(=O)—, or CH₃CH₂OC(=O)—;

Ring B is

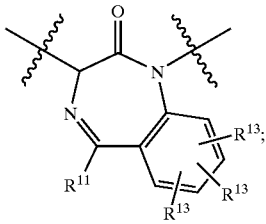

$R^{11}$, at each occurrence, is independently selected from H, $NR^{18}R^{19}$;
  C₁–C₄ alkyl optionally substituted with 0–1 $R^{11a}$;
  phenyl substituted with 0–3 $R^{11b}$;
  5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, CF₃, or phenyl substituted with 0–3 $R^{11b}$;

$R^{11b}$, at each occurrence, is independently selected from H, OH, Cl, F, $NR^{15}R^{16}$, CF₃, methyl, ethyl, propyl, butyl, methoxy, ethoxy, propoxy, C₁–C₂ haloalkyl, and C₁–C₂ haloalkoxy;

W is a bond;
X is a bond;
Y is a bond;
Z is H;

84

C₁–C₄ alkyl substituted with 0–1 $R^{12a}$;
  C₂–C₄ alkenyl substituted with 0–1 $R^{12a}$; or
  C₂–C₄ alkynyl substituted with 0–1 $R^{12a}$;

$R^{12a}$, at each occurrence, is independently selected from H, OH, Cl, F, $NR^{15}R^{16}$, CF₃, acetyl, SCH₃, S(=O)CH₃, S(=O)₂CH₃, methyl, ethyl, propyl, butyl, methoxy, ethoxy, propoxy, C₁–C₂ haloalkyl, and C₁–C₂ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and CF₃;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

provided when Q is —NH—R⁴, then R⁴ does not contain a —C(=O)— adjacent to —N($R^{7b}$)—.

7. A compound according to claim 6 wherein:

R⁵ and $R^{5a}$ are combined to form cyclopentyl or cyclohexyl;

Q is
  —CH₂CH₃,
  —CH₂CH₂CH₃,
  —CH₂CH₂CH₂CH₃,
  —CH₂CH₂CH₂CH₂CH₃,
  —CH₂CH₂CH₂CH₂CH₂CH₃,
  —CH₂CH(CH₃)₂,
  —CH₂CH₂CH(CH₃)₂,
  —CH₂CH₂CH₂CH(CH₃)₂'
  —CH₂CH₂CH₂CH₂CH(CH₃)₂ᵃ
  —CH₂NHCH₂CH₃,
  —CH₂NHCH₂CH₂CH₃,
  —CH₂NHCH₂CH₂CH₂CH₃,
  —CH₂NHCH(CH₃)₂,
  —CH₂NHCH₂CH(CH₃)₂,
  —CH₂NHCH₂CH₂CH(CH₃)₂—,
  —CH₂CH(OH)CH₂CH₃,
  —CH₂CH(OH)CH₂CH₂CH₃,
  —CH₂CH(OH)CH₂CH₂CH₂CH₃,
  —CH₂CH(OH)CH(CH₃)₂,
  —CH₂CH(OH)CH₂CH(CH₃)₂,
  —CH₂CF(cyclopropyl),
  —CH₂CH₂CH(cyclopropyl)
  —CH₂CH₂CH₂CH(cyclopropyl),
  —CH₂N (C(=O)OCH₂CH₃)CH₂CH₂CH(CF₃)₂,
  —CH₂NHC(=O)—CH₂-(3,5-diF-phenyl),
  —CH₂NHC(=O)CH(OH)CH(CH₃)₂,
  —CH₂NHC(=O)CH(OH)CH₂CH(CH₃)₂,
  —CH₂NHC(=O)CH(OH)CH₂CH₂CH₃,
  —CH₂NHCH₂CH(OH)CH₂CH(CH₃)₂,
  —CH₂NHCH₂CH(OH)CH₂CH₂CH₃,
  —CH₂NHCH₂CH(OH)CH₂CH₂CH₂CH₃,
  —CH₂NHCH₂CH(OH)CF(CH₃)₂,
  —CH₂NHCH₂CH₂-(cyclopropyl),
  —CH₂NHCH₂CH₂-(cyclobutyl),
  —CH₂NHCH₂CH₂-(cyclopentyl),
  —CH₂NHCH₂CH₂- cyclohexyl),
  —CH₂NHCH₂-(cyclopropyl),
  —CH₂NHCH₂-(cyclobutyl),
  —CH₂NHCH₂-(cyclopentyl), —CH₂NHCH₂-(cyclohexyl),
—CH₂NH-(cyclopropyl),
—CH₂NH-(cyclobutyl),
—CH₂NH-(cyclopentyl),
—CH₂NH-(cyclohexyl),
—CH₂NHCH₂CH₂-(3,5-diF-phenyl),
—CH₂NHCH₂-(1,4-diF-phenyl),
—CH₂CH₂NHCH₂CH(CH₃)₂,
—CH₂CH₂NHCH₂CH₂CH₃,
—CH₂CH₂NHCH₂CH₂CH₂CH₃,
—CH₂CH₂NHCH₂-(cyclopropyl),
—CH₂CH₂NHCH₂-(cyclobutpyl),
—CH₂CH₂NHCH₂-(cyclopentyl),
—CH₂CH₂NHCH₂-(cyclohexyl),
—NHCH₂CH(OH)CH(CH₃)₂,
—NHCH₂CH(OH)-(cyclopropyl),
—NHCH₂CH(OH)-(cyclobutyl),
—NHCH₂CH(OH)-(cyclopentyl),
—NHCH₂CH(OH)-(cyclohexyl), or
—CH₂NHCH₂CH(OH)-(phenyl);

W is a bond;
X is a bond;
Y is a bond;
Z is methyl, ethyl, i-propyl, n-propyl, n-butyl, i-butyl, s-butyl, t-butyl, or allyl;
$R^{11}$, at each occurrence, is independently selected from H, methyl, ethyl, phenyl, benzyl, phenethyl, 4-F-phenyl, (4-F-phenyl)$CR^2$—, (4-F-phenyl)$CR^2CH_2$—, 3-F-phenyl, (3-F-phenyl)CH₂—, (3-F-phenyl)CH₂CH₂—, 2-F-phenyl, (2-F-phenyl)$CR^2$—, (2-F-phenyl)CH₂$CR^2$—, 4-Cl-phenyl, (4-Cl-phenyl)CH₂—, (4-Cl-phenyl)CH₂CH₂—, 3-Cl-phenyl, (3-Cl-phenyl)$CR^2$—, (3-Cl-phenyl)CH₂$CR^2$—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-$CR^3$-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, or pyrid-4-yl; and
$R^{13}$, at each occurrence, is independently selected from H, F, Cl, OH, —$CR^3$, —$CR^2CH_3$, —$OCR^3$, and —CF₃.

8. A compound, according to claim 2, wherein:
$R^5$ and $R^{5a}$ are combined to form cyclopentyl or cyclohexyl;
Q is
—$CR^2CR^3$,
—CH₂CH₂CH₃,
—CH₂CH₂CH₂CH₃,
—CH₂CH₂CH₂CH₂CH₃,
—CH₂CH₂CH₂CH₂CH₂CH₃,
—CH₂CH(CH₃)₂,
—CH₂CH₂CH(CH₃)₂,
—CH₂CH₂CH₂CH(CH₃)₂,
—CH₂CH₂CH₂CH₂CH(CH₃)₂,
—CH₂NHCH₂CH₃,
—CH₂NHCH₂CH₂CH₃,
—CH₂NHCH₂CH₂CH₂CH₃,
—CH₂NHCH(CH₃)₂,
—CH₂NHCH₂CH(CH₃)₂,
—CH₂NHCH₂CH₂CH(CH₃)₂,
—CH₂CH(OH)CH₂CH₃,
—CH₂CH(OH)CH₂CH₂CH₃,
—CH₂CH(OH)CH₂CH₂CH₂CH₃,
—CH₂CH(OH)CH(CH₃)₂,
—CH₂CH(OH)CH₂CH (CH₃)₂,
—CH₂CH(OH)CH₂CH₂CH(CH₃)₂,
—CH₂CH(cyclopropyl),
—CH₂CH₂CH(cyclopropyl),
—CH₂CH₂CH₂CH(cyclopropyl),
—CH₂N(C(=O)OCH₂CH₃)CH₂CH₂CH(CH₃)₂,
—CH₂NHC(=O) —CH₂-(3,5-diF-phenyl)
—CH₂NHC(=O)CH(OH)CH(CH₃)₂,
—CH₂NHC(=O)CH(OH)CH₂CH(CH₃)₂,
—CH₂NHC(=O)CH(OH)CH₂CH₂CH₃,
—CH₂NHCH₂CH(OH)CH₂CH(CH₃)₂,
—CH₂NHCH₂CH(OH)CH₂CH₂CH₃,
—CH₂NHCH₂CH(OH)CH₂CH₂CH₂CH₃.
—CH₂NHCH₂CH(OH)CH(CH₃)₂.
—CH₂NHCH₂CH₂-(cyclopropyl),
—CH₂NHCH₂CH₂-(cyclobutyl).
—CH₂NHCH₂CH₂-(cyclopentyl),
—CH₂NHCH₂CH₂-(cyclohexyl),
—CH₂NHCH₂-(cyclopropyl),
—CH₂NHCH₂-(cyclobutyl),
—CH₂NHCH₂-(cyclopentyl),
—CH₂NHCH₂-(cyclohexyl),
—CH₂NH-(cyclopropyl),
—CH₂NH-(cyclobutyl),
—CH₂NH-(cyclopentyl),
—CH₂NH-(cyclohexyl),
—CH₂NHCH₂CH₂-(3,5-diF-phenyl),
—CH₂NHCH₂-(1,4-diF-phenyl),
—CH₂CH₂NHCH₂CF(CH₃)₂,
—CH₂CH₂NHCH₂CH₂CH₃,
—CH₂CH₂NHCH₂CH₂CH₂CH₃,
—CH₂CH₂NHCH₂-(cyclopropyl),
—CH₂CH₂NHCH₂-(cyclobutpyl),
—CH₂CH₂NHCH₂-(cyclopentyl),
—CH₂CH₂NHCH₂-(cyclohexyl),
—NHCH₂CH(OH)CF(CH₃)₂,
—NHCH₂CH(OH)-(cyclopropyl),
—NHCH₂CH(OH)-(cyclobutyl),
—NHCH₂CH(OH)-(cyclopentyl),
—NHCH₂CH(OH)-(cyclohexyl), or
—CH₂NHCH₂CH(OH)-(phenyl);

W is a bond or —CH₂—;
X is a bond;

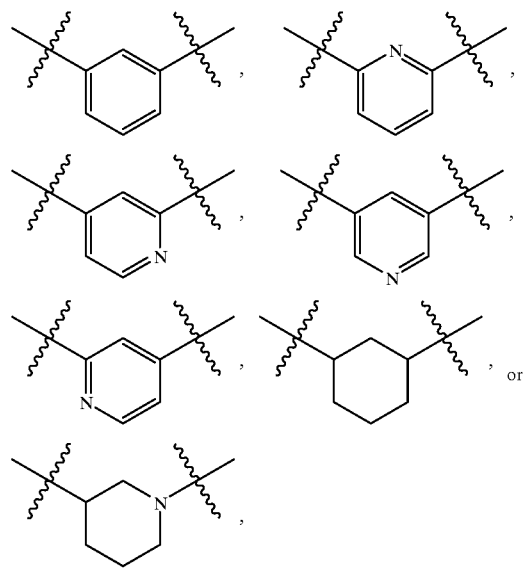

Y is a bond, —C(=O)—, —O—, —S—, —S(=O)—, —S(=O)₂—, —NH—, or —N(CH₃)—,
Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4- diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_{3O}$-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl-4$CH_2$—, (3-Cl-4-F-phenyl)$CH_2$—, (2-MeO-phenyl )$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3$O-phenyl)$CH_2$—, (3-$CF_{3O}$-phenyl)$CH_2$—, (4-$CF_3$O-phenyl)$CH_2$—, (furanyl)$CH_2$—, (thienyl)$CH_2$—, (pyridyl)$CH_2$—, (2-Me-pyridyl)$CH_2$—, (3-Me-pyridyl)$CH_2$-, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, (cyclopropyl)$CH_2$—, (cyclobutyl)$CH_2$—, (cyclopentyl)$CH_2$—, (cyclohexyl)$CH_2$—, (morpholino)$CH_2$—, (N-pipridinyl)$CH_2$—, phenyl-$CH_2CH_2$—, (phenyl)$CHCH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-$C_1$-phenyl)$CH_2CH_2$—, (3-Cl-4-F-phenyl)$CH_2CH_2$—, (2-MeO-phenyl)$CH_2CH_2$—, (3-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_{3O}$-phenyl)$CH_2CH_2$—, (3-$CF_{3O}$-phenyl)$CH_2CH_2$—, (4-$CF_{3O}$-phenyl)$CH_2CH_2$—, (furanyl-4$CH_2CH_2$—, (thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$—, (cyclopropyl)$CH_2CH_2$—, (cyclobutyl)$CH_2CH_2$—, (cyclopentyl)$CH_2CH_2$—, (cyclohexyl)$CH_2CH_2$—, (morpholino)$CH_2CH_2$—, or (N-pipridinyl)$CH_2CH_2$—;

$R^{11}$, at each occurrence, is independently selected from H, methyl, ethyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-$CH_3$-phenyl, (4-Cl-phenyl)$CH_2$—, (4-Cl-phenyl)$CH_2CH_2$—, 3-$CH_3$-phenyl, (3-Cl-phenyl)$CH_2$—, (3-Cl-phenyl)$CH_2CH_2$—, 4-$CF_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, pyrid-2-yl, pyrid-3—yl, or pyrid-4-yl; and $R^{13}$, at each occurrence, is independently selected from H, F, Cl, OH, —$CH_3$, —$CH_2CH_3$, —$OCH_3$, and —$CF_3$.

9. A compound according to one of claims 1, 2, 3, 4, 5, 6, 7, or 8 of Formula (Id):

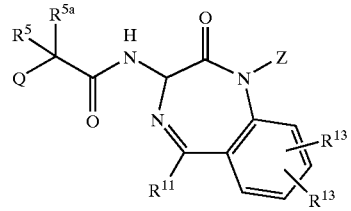

(Id)

or a stereoisomer or a pharmaceutically acceptable salt thereof.

10. A compound according to claim 1 selected from:
1-{[(3-methylbutylamino]methyl}-N-{(S)-1,3-dihydro-1-methyl-2-oxo-5-[4-(trifluoromethyl)phenyl]-2H-1,4-benzodiazepin-3 -yl}-cyclopentanecarbocylic amide;
1-(5-methyl)hexyl-N-{(S)-1,3-dihydro-1-methyl-2-oxo-5-phenyl-2H-1,4-benzodiazepin-3-yl}-cyclopentanecarbocylic amide;
1-pentyl-N-{(S)-1,3-dihydro-1-methyl-2-oxo-5-phenyl-2H-1,4-benzodiazepin-3-yl}-cyclopentanecarbocylic amide;
1-(2-hydroxypentyl)-N-{(S)-1,3-dihydro-1-methyl-2-oxo-5-phenyl-2H-1,4-benzodiazepin-3-yl}-cyclopentanecarbocylic amide;
2-(S)-hydroxy-3-methyl-N-{[(N-{1-methyl-2-oxo-5-[4-(trifluoromethyl)phenyl](3H-benzo[f]1,4-diazepin-3-yl)}carbamoyl)cyclopentyl]methyl}butanamide;
(2S)-N-({[N-(7-fluoro-1-methyl-2-oxo-5-phenyl(3H-benzo[f]1,4-diazepin-3-yl))carbamoyl]cyclopentyl}methyl)-2-hydroxy-3-methylbutanamide;
(2S)-N-({[N-(5-cyclopentyl-1-methyl-2-oxo(3H-benzo[f]1,4-diazepin-3-yl))carbamoyl]cyclopentyl}methyl)-2-hydroxy-3-methylbutanamide;
({[(2-hydroxyhexyl)amino]methyl}cyclopentyl)-N-{1-methyl-2-oxo-5-[4-(trifluoromethyl)phenyl](3H-benzo[f]1,4-diazepin-3-yl)}carboxamide;
({[((2R)-2-hydroxy-2-phenylethyl)amino]methyl}cyclopentyl)-N-{1-methyl-2-oxo-5-[4-(trifluoromethyl)phenyl](3H-benzo[f]1,4-diazepin-3-yl)}carboxamide; and
({[((2S)-2-hydroxy-2-phenylethyl)amino]methyl}cyclopentyl)-N-{1-methyl-2-oxo-5-[4-(trifluoromethyl)phenyl](3H- benzo[f]1,4-diazepin-3-yl)}carboxamide.

11. A pharmaceutical composition comprising a compound of claim 1 and a pharmaceutically acceptable carrier.
12. A pharmaceutical composition comprising a compound of claim 2 and a pharmaceutically acceptable carrier.
13. A pharmaceutical composition comprising a compound of claim 3 and a pharmaceutically acceptable carrier.
14. A pharmaceutical composition comprising a compound of claim 4 and a pharmaceutically acceptable carrier.
15. A pharmaceutical composition comprising a compound of claim 5 and a pharmaceutically acceptable carrier.

16. A pharmaceutical composition comprising a compound of claim 6 and a pharmaceutically acceptable carrier.

17. A pharmaceutical composition comprising a compound of claim 7 and a pharmaceutically acceptable carrier.

18. A pharmaceutical composition comprising a compound of claim 8 and a pharmaceutically acceptable carrier.

19. A pharmaceutical composition comprising a compound of claim 9 and a pharmaceutically acceptable carrier.

20. A pharmaceutical composition comprising a compound of claim 10 and a pharmaceutically acceptable carrier.

21. A method for the treatment of Alzheimer's Disease comprising administering to a host in need of such treatment a therapeutically effective amount of a compound of claim 1.

22. A method for the treatment of Alzheimer's Disease comprising administering to a host in need of such treatment a therapeutically effective amount of a compound of claim 2.

23. A method for the treatment of Alzheimer's Disease comprising administering to a host in need of such treatment a therapeutically effective amount of a compound of claim 3.

24. A method for the treatment of Alzheimer's Disease comprising administering to a host in need of such treatment a therapeutically effective amount of a compound of claim 4.

25. A method for the treatment of Alzheimer's Disease comprising administering to a host in need of such treatment a therapeutically effective amount of a compound of claim 5.

26. A method for the treatment of Alzheimer's Disease comprising administering to a host in need of such treatment a therapeutically effective amount of a compound of claim.

27. A method for the treatment of Alzheimer's Disease comprising administering to a host in need of such treatment a therapeutically effective amount of a compound of claim 7.

28. A method for the treatment of Alzheimer's Disease comprising administering to a host in need of such treatment a therapeutically effective amount of a compound of claim 8.

29. A method for the treatment of Alzheimer's Disease comprising administering to a host in need of such treatment a therapeutically effective amount of a compound of claim 9.

30. A method for the treatment of Alzheimer's Disease comprising administering to a host in need of such treatment a therapeutically effective amount of a compound of claim 10.

* * * * *